US012351824B2

(12) United States Patent
Qian et al.

(10) Patent No.: US 12,351,824 B2
(45) Date of Patent: Jul. 8, 2025

(54) METHOD FOR PRODUCING NATURAL KILLER CELLS FROM PLURIPOTENT STEM CELLS

(71) Applicant: Takeda Pharmaceutical Company Limited, Osaka (JP)

(72) Inventors: Yu Qian, Cambridge, MA (US); Hui-Hsin Chang, Cambridge, MA (US); Xi Shi, Cambridge, MA (US); Jianxin Hu, Cambridge, MA (US); Lan Cao, Cambridge, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 859 days.

(21) Appl. No.: 17/186,877

(22) Filed: Feb. 26, 2021

(65) Prior Publication Data

US 2021/0292713 A1    Sep. 23, 2021

Related U.S. Application Data

(60) Provisional application No. 62/983,511, filed on Feb. 28, 2020.

(51) Int. Cl.
| | | |
|---|---|---|
| *C12N 5/0783* | (2010.01) | |
| *A61K 40/15* | (2025.01) | |
| *A61K 40/31* | (2025.01) | |
| *A61K 40/35* | (2025.01) | |
| *A61K 40/42* | (2025.01) | |
| *C07K 14/54* | (2006.01) | |
| *C07K 14/705* | (2006.01) | |
| *C07K 14/725* | (2006.01) | |
| *C07K 16/28* | (2006.01) | |

(52) U.S. Cl.
CPC ............ *C12N 5/0646* (2013.01); *A61K 40/15* (2025.01); *A61K 40/31* (2025.01); *A61K 40/35* (2025.01); *A61K 40/4211* (2025.01); *C07K 14/5443* (2013.01); *C07K 14/705* (2013.01); *C07K 14/7051* (2013.01); *C07K 14/70517* (2013.01); *C07K 14/70578* (2013.01); *C07K 16/2803* (2013.01); *A61K 2239/31* (2023.05); *A61K 2239/38* (2023.05); *A61K 2239/48* (2023.05); *C07K 2319/03* (2013.01); *C12N 2500/02* (2013.01); *C12N 2501/115* (2013.01); *C12N 2501/125* (2013.01); *C12N 2501/155* (2013.01); *C12N 2501/165* (2013.01); *C12N 2501/2302* (2013.01); *C12N 2501/2307* (2013.01); *C12N 2501/26* (2013.01); *C12N 2501/515* (2013.01); *C12N 2501/998* (2013.01); *C12N 2501/999* (2013.01); *C12N 2506/45* (2013.01)

(58) Field of Classification Search
CPC ............ C07K 16/2803; C07K 2319/03; C12N 2500/02; C12N 2501/115; C12N 2501/125; C12N 2501/155; C12N 2501/165; C12N 2501/2302; C12N 2501/2307; C12N 2501/26; C12N 2501/515; C12N 2501/998; C12N 2501/999; C12N 2506/45

See application file for complete search history.

(56) References Cited

U.S. PATENT DOCUMENTS

| 11,578,310 B2 * | 2/2023 | Kaneko .......... A61K 39/464474 |
| 2017/0107492 A1 | 4/2017 | Yu et al. |
| 2018/0187156 A1 * | 7/2018 | Rossi ...................... A61P 1/04 |
| 2018/0305664 A1 * | 10/2018 | Vodyanyk ............ C12N 5/0639 |
| 2019/0330596 A1 | 10/2019 | Kaneko et al. |

FOREIGN PATENT DOCUMENTS

| CN | 108350429 A | 7/2018 |
| CN | 109415699 A | 3/2019 |
| WO | 2011/080740 A1 | 7/2011 |
| WO | 2016/123100 A1 | 8/2016 |
| WO | WO 2017/078807 A1 | 5/2017 |
| WO | WO-2017221975 A1 * | 12/2017 ......... A61K 39/0011 |
| WO | 2018/195175 A1 | 10/2018 |

OTHER PUBLICATIONS

Zeng et al ("Generation of "Off-the-Shelf" Natural Killer Cells from Peripheral Blood Cell-Derived Induced Pluripotent Stem Cells," Stem Cell Reports vol. 9 1796-1812 Dec. 12, 2017 (Year: 2017).*
Zeng supplemental experimental procedures from "Generation of "Off-the-Shelf" Natural Killer Cells from Peripheral Blood Cell-Derived Induced Pluripotent Stem Cells," Stem Cell Reports vol. 9 1796-1812 Dec. 12, 2017 (Year: 2017).*
Eguizabal et al ("Natural killer cells for cancer immunotherapy: pluripotent stem cells-derived NK cells as an immunotherapeutic perspective," Front. Immunol., Sep. 15, 2014) (Year: 2014).*
Li, Y. et al., "Human iPSC-Derived Natural Killer Cells Engineered with Chimeric Antigen Receptors Enhance Anti-Tumor Activity", Cell Stem Cell, vol. 23, No. 2, Jun. 28, 2018, pp. 181-192.
Zeng, J. et al., "Generation of "Off-the-Shelf" Natural Killer Cells from Peripheral Blood Cell-Derived Induced Pluripotent Stem Cells", Stem Cell Reports, vol. 9, No. 6, Dec. 12, 2017, pp. 1796-1812.
Bernarreggi, D. et al., "Development of innate immune cells from human pluripotent stem cells", Experimental Hematalogy, vol. 71, Mar. 1, 2019, pp. 13-23.
Eguizabal, C. et al., "Natural Killer Cells for Cancer Immunotherapy: Pluripotent Stem Cells-Derived NK Cells as an Immunotherapeutic Perspective", Frontiers in Immunology, vol. 5, Sep. 15, 2014, pp. 1-10.
International Search Report for PCT/US2021/019917, 4 pages, (dated Jun. 11, 2021).

(Continued)

*Primary Examiner* — Marcia S Noble

(74) *Attorney, Agent, or Firm* — Proskauer Rose LLP

(57) ABSTRACT

The present disclosure provides, among other things, a method for efficiently producing natural killer cells from induced pluripotent cells. The method includes the steps of: (I) culturing pluripotent stem cells in a culture medium to produce CD56+/CD3− immune cells.

16 Claims, 3 Drawing Sheets

(56) References Cited

OTHER PUBLICATIONS

Carlens, et al., "A New Method for in Vitro Expansion of Cytotoxic Human CD3-CD56+ Natural Killer Cells", Hum Immunology, Oct. 2001, vol. 62, Issue 10, Oct. 2001, (10):1092-8. doi: 10.1016/s0198-8859(01)00313-5.PMID: 11600215 DOI: 10.1016/s0198-8859(01)00313-5, pp. 1092-1098 (7 pages).
International Search Report for PCT/IB2022/055504 dated Oct. 28, 2022 (4 pages).
Taiwanese Search Report for Application No. 110107162 dated Oct. 8, 2024 (2 pages).
Zhu, et al., "Engineered Human Pluripotent Stem Cell-Derived Natural Killer Cells: The Next Frontier for Cancer Immunotherapy", Blood Science, Sep. 17, 2019. 1(1):4-11. doi: 10.1097/BS9.0000000000000023. eCollection Aug. 2019 (8 pages).

\* cited by examiner

METHOD FOR PRODUCING NATURAL KILLER CELLS FROM PLURIPOTENT STEM CELLS

RELATED APPLICATIONS

This application claims priority to U.S. Provisional Application Ser. No. 62/983,511, filed Feb. 28, 2020, the disclosure of which is hereby incorporated by reference.

BACKGROUND

Natural Killer (NK) cells are cytotoxic lymphocytes of the immune system. NK cells are cytotoxic against cancerous, pathogen-infected and otherwise damaged cells. NK cells are innate lymphoid cells (ILCs), specifically large granular cytotoxic lymphocytes that bridge the innate and the adaptive arms of the immune response. They make up 10-15% of circulating lymphocytes in the peripheral blood. NK cells also exhibit the highest level of cytotoxic activity within the immune system. Therefore, altered NK cell functionality or numbers impact the functioning of the immune system against infection and cancer.

NK cells lack specific cell surface antigen receptors. Because of this, NK cells may kill cancerous and pathogen-infected cells without prior sensitization, making them part of the innate immune response. They also have a role in tumor immunosurveillance by directly influencing the adaptive immune response. These features and others make NK cells a particularly attractive cell type for use in adoptive cell therapies.

Various protocols have been described to obtain NK cells from progenitor cells. However, the previously described protocols are labor intensive and require multiple, time consuming steps, including steps of cell isolation which in turn increases manufacturing/production time and monetary cost to produce NK cells.

SUMMARY

The present application provides, among other things, improved methods of producing CD56+/CD3− immune cells (i.e., NK or NK-like cells). This application is based, at least in part, on the surprising discovery of efficient and robust production of CD56+/CD3− immune cells from a bulk cell population derived from pluripotent stem cells (e.g., induced pluripotent stem cells (iPSCs)) without the need for a cell isolation step. Prior to the present application, methods for inducing NK cells often require isolation of particular cell types based on known cell lineages to NK cells. As described herein, the present application unexpectedly shows that NK cells can be successfully derived from a bulk cell population without requiring isolation of any cell types based on lineages. This method thus has numerous benefits over existing methods of producing NK cells, including for example, the ability to scale up and produce large quantities of NK cells in a cost and time efficient manners. Thus the present invention represents a significant breakthrough in the cell therapy field.

iPSC-derived CD56+/CD3− cells (also referred to herein as "iNK cells") produced by the methods described herein are functional and can be further genetically modified, such as through the introduction of CAR to target specific cell populations.

In some aspects, a method of producing pluripotent stem cell-derived NK cells is provided comprising: (A) providing a bulk cell population comprising hematopoietic progenitor cells (HPC) (HP cell bulk) derived from pluripotent stem cells. (B) culturing the HP cell bulk in one or more culture medium to produce CD56+/CD3− cells, wherein the method does not include a cell isolation step.

In some embodiments, the method does not include a cell isolation step in step (A) and (B).

In some embodiments, the HP cell bulk in (A) comprises CD34+ cells.

In some embodiments, 20% or more of the cells in the HP cell bulk are CD34+ cells.

In some embodiments, between 20% and 90% of the HP cell bulk are CD34+ cells. For example, in some embodiments, about 30% of the HP cell bulk are CD34+ cells. In some embodiments, about 40% of the HP cell bulk are CD34+ cells. In some embodiments, about 50% of the HP cell bulk are CD34+ cells. In some embodiments, about 60% of the HP cell bulk are CD34+ cells. In some embodiments, about 70% of the HP cell bulk are CD34+ cells. In some embodiments, about 80% of the HP cell bulk are CD34+ cells. In some embodiments, about 90% of the HP cell bulk are CD34+ cells. In some embodiments, greater than 70% of the HP cell bulk are CD34+ cells.

In some embodiments, step (B) comprises (i) culturing the HP cell bulk in CD4/CD8 induction media to generate an intermediate heterogeneous cell population comprising CD4−/CD8− cells, CD4−/CD8+ cells, CD4+/CD8−, and CD4+/CD8+ cells; and (ii) culturing the intermediate heterogeneous cell population in NK induction media to produce the CD56+/CD3− cells.

In some embodiments, step (A) comprises culturing pluripotent stem cells in HPC induction media to produce HP cell bulk.

In some embodiments, the pluripotent stem cells are induced pluripotent stem cell (iPSC).

In some embodiments, the HPC induction media comprises at least one compound, or any combination of compounds, selected from bone morphogenetic protein-4 (BMP4) vascular endothelial growth factor (VEGF), basic fibroblast growth factor (bFGF), ascorbic acid, Flt3 ligand (Flt3L), thrombopoietin (TPO) and TGFβ inhibitor.

In some embodiments, the HPC induction media comprises BMP4 at a concentration of between 5 ng/mL to 500 ng/ml.

In some embodiments, the BMP4 is at a concentration of 50 ng/ml.

In some embodiments, the HPC induction media comprises VEGF at a concentration of between 5 ng/ml to 500 ng/ml.

In some embodiments, the VEGF is at a concentration of about 50 ng/ml.

In some embodiments, the HPC induction media comprises bFGF at a concentration of between 5 ng/ml to 500 ng/ml.

In some embodiments, the bFGF is at a concentration of 50 ng/ml.

In some embodiments, the HPC induction media comprises ascorbic acid at a concentration of between 5 μg/ml and 500 μg/ml.

In some embodiments, the ascorbic acid is at a concentration of 50 μg/ml.

In some embodiments, the HPC induction media comprises Flt3L at a concentration between 1 ng/ml to 100 ng/ml.

In some embodiments, the Flt3L is at a concentration of 50 ng/ml.

In some embodiments, the HPC induction media comprises TPO at a concentration of between 1 ng/ml to 200 ng/ml.

In some embodiments, the TPO is at a concentration of 100 ng/ml.

In some embodiments, the CD4/CD8 induction media comprises at least one compound, or any combination of compounds, selected from the group consisting of ascorbic acid, stem cell factor (SCF), IL-7, Flt3L, thrombopoietin (TPO), p38 inhibitor and SDF-1. Accordingly, in some embodiments, the CD4/CD8 induction media comprises ascorbic acid. In some embodiments, the CD4/CD8 induction media comprises SCF. In some embodiments, the CD4/CD8 induction media comprises IL-7. In some embodiments, the CD4/CD8 induction media comprises Flt3L. In some embodiments, the CD4/CD8 induction media comprises TPO. In some embodiments, the CD4/CD8 induction media comprises p38 inhibitor. In some embodiments, the CD4/CD8 induction media comprises SDF-1. In some embodiments, the CD4/CD8 induction media comprises p38 inhibitor and SDF-1.

In some embodiments, the CD4/CD8 induction media comprises ascorbic acid at a concentration between 5 μg/ml to about 500 μg/ml.

In some embodiments, the ascorbic acid is at a concentration of 50 μg/ml.

In some embodiments, the CD4/CD8 induction media comprises SCF at a concentration between 5 ng/ml to 100 ng/ml.

In some embodiments, the SCF is at a concentration 50 ng/ml.

In some embodiments, the CD4/CD8 induction media comprises IL-7 at a concentration between 1 ng/ml to 100 ng/ml.

In some embodiments, the IL-7 is at a concentration of 50 ng/ml.

In some embodiments, the CD4/CD8 induction media comprises Flt3L at a concentration of between 1 ng/ml to 100 ng/ml.

In some embodiments, the Flt3L at a concentration of 50 ng/ml Flt3L.

In some embodiments, the CD4/CD8 induction media comprises TPO at a concentration between 1 ng/ml to 200 ng/ml.

In some embodiments, the TPO is at a concentration of 100 ng/ml.

In some embodiments, the CD4/CD8 induction media comprises p38 inhibitor at a concentration between 0.5 μM to 100 μM.

In some embodiments, the p38 inhibitor is SB203580. In some embodiments, the p38 inhibitor is BIRB 796. In some embodiments, the p38 inhibitor is VX-702. In some embodiments, the p38 inhibitor is SB239063. In some embodiments, the p38 inhibitor is SB202190. In some embodiments, the p38 inhibitor is BMS 582949.

In some embodiments, the SB203580 is at a concentration of 15 μM.

In some embodiments, the CD4/CD8 induction media comprises SDF-1 inhibitor at a concentration between 10 ng/ml to about 100 ng/ml.

In some embodiments, the SDF-1 inhibitor is at a concentration of 30 nM.

In some embodiments, the SDF-1 inhibitor is at a concentration of 30 nM and the p38 inhibitor, e.g., SB203580, is at a concentration of 15 μM.

In some embodiments, the NK induction media comprises at least one compound selected from the group consisting of a CD3 activator, IL-2 and IL7. Accordingly, in some embodiments, the NK induction media comprises CD3 activator. In some embodiments, the NK induction media comprises IL-2. In some embodiments, the NK induction media comprises IL-7.

In some embodiments, the NK induction media comprises IL-2 at a concentration of between 1 ng/ml to 100 ng/ml.

In some embodiments, the IL-2 is at a concentration of 10 ng/ml.

In some embodiments, the NK induction media comprises IL-7 at a concentration between 1 ng/ml to 100 ng/ml.

In some embodiments, the IL-7 is at a concentration of 10 ng/ml.

In some embodiments, each of the culturing step is performed at about 5% oxygen.

In some embodiments, each of the culturing step is performed at greater than 14% oxygen.

In some embodiments, each of the culturing step is performed at atmospheric oxygen.

In some embodiments, each of the culturing step is performed at less than 5% oxygen.

In some embodiments, culturing pluripotent stem cells in the bulk cell medium to obtain HP cell bulk lasts for greater than 10 days.

In some embodiments, culturing pluripotent stem cells in the bulk cell medium to obtain HP cell bulk lasts between 11 and 15 days.

In some embodiments, culturing pluripotent stem cells in the bulk cell medium to obtain HP cell bulk lasts for 14 days.

In some embodiments, the iPSC are obtained from peripheral blood mononuclear cells.

In some embodiments, at least about 50%, 55%, 60%, 75%, 80%, 85%, 90%, 95%, 97% or more of produced cells are CD56+/CD3− cells without a step of enrichment, e.g., without a further step of sorting/isolation/purification of CD56+/CD3− cells. Accordingly, in some embodiments, at least about 50% or more of produced cells are CD56+/CD3− cells without a step of enrichment. In some embodiments, at least about 55% or more of produced cells are CD56+/CD3− cells without a step of enrichment. In some embodiments, at least about 60% or more of produced cells are CD56+/CD3− cells without a step of enrichment. In some embodiments, at least about 65% or more of produced cells are CD56+/CD3− cells without a step of enrichment. In some embodiments, at least about 70% or more of produced cells are CD56+/CD3− cells without a step of enrichment. In some embodiments, at least about 75% or more of produced cells are CD56+/CD3− cells without a step of enrichment. In some embodiments, at least about 80% or more of produced cells are CD56+/CD3− cells without a step of enrichment. In some embodiments, at least about 85% or more of produced cells are CD56+/CD3− cells without a step of enrichment. In some embodiments, at least about 90% or more of produced cells are CD56+/CD3− cells without a step of enrichment. In some embodiments, at least about 95% or more of produced cells are CD56+/CD3− cells without a step of enrichment. In some embodiments, at least about 97% or more of produced cells are CD56+/CD3− cells without a step of enrichment.

In some embodiments, less than about 25%, 20%, 15%, 10% or 5% of produced cells are CD3+ cells.

In some embodiments, the phenotype of the produced cells can be ascertained by various means in the art. For example, the phenotype of the produced cells can be ascertained by flow cytometry or single-cell RNA sequencing (scRNAseq).

In some embodiments, the percentage of produced cells is determined by flow cytometry. In some embodiments, the percentage of produced cells is determined by scRNAseq.

In some embodiments, the method further comprises a step of isolating CD56+/CD3− cells.

In some embodiments, CD56+/CD3− cells are isolated by fluorescence-activated cell sorting (FACS) or magnetic sorting. Accordingly, in some embodiments, the cells are isolated by FACS. In some embodiments, the cells are isolated by magnetic sorting (MACS).

In some embodiments, the CD56+/CD3− immune cells are NK cells.

In some embodiments, the CD56+/CD3− cells are genetically modified to express one or more chimeric antigen receptors (CAR).

In some embodiments, the isolated CD56+/CD3− cells are genetically modified to express one or more chimeric antigen receptors (CAR).

In some embodiments, the antigen is CD19.

In some embodiments, the cells are further genetically modified to express IL-15Rα/IL-15 complex.

In some aspects, a method of producing induced pluripotent stem cell (iPSC)-derived CD56+/CD3− immune cells is provided comprising the following steps: (1) culturing iPSC in HPC induction media comprising at least one compound selected from vascular endothelial growth factor (VEGF), basic fibroblast growth factor (bFGF), and ascorbic acid to obtain a heterogeneous population of cells comprising hematopoietic progenitor cells (HPC) (HP cell bulk); (2) culturing the HP cell bulk obtained in (1) in CD4/CD8 induction media comprising one or more of ascorbic acid, p38 inhibitor and SDF-1 to obtain an intermediate heterogeneous population of cells; and (3) culturing the intermediate heterogeneous population of cells from (2) in NK induction media comprising at least one compound selected from the group consisting of a CD3 activator, IL-2 and IL-7.

In some aspects, an NK cell population is provided, the population produced using a method described herein.

In some aspects, an unsorted cell population is provided, the population comprising pluripotent stem cell-derived CD56+/CD3− cells at a ratio of not less than 60% of total pluripotent stem cell-derived CD56+ immune cells.

In some embodiments, less than 25% of cells are CD3+ cells.

In some embodiments, less than 5% of cells are monocytes.

In some embodiments, less than 5% of cells are B cells.

In some aspects, a method of treating a subject in need of cell therapy is provided, the method comprising administering to the subject the NK cells described herein.

In some embodiments, the subject has a cancer.

In some embodiments, the cancer is leukemia or lymphoma.

In some aspects, a method of producing pluripotent cell-derived CD56+/CD3− immune cells is provided, said method comprising the step of (I) culturing a pluripotent stem cell in one or more culture medium to produce CD56+/CD3− immune cells.

In some embodiments, step (I) comprises: (A) culturing a pluripotent stem cell in a culture medium to produce hematopoietic progenitor cells (HPC) (HP cell bulk); and (B) culturing the cells obtained in step (A) in a culture medium to produce CD56+/CD3− immune cells.

In some embodiments, step (B) comprises: (a) culturing the cells obtained in step (A) in a culture medium to produce a cell population comprising CD4/CD8 double-positive cells; and (b) culturing the cells obtained in step (a) in a culture medium to produce CD56+/CD3− immune cells.

In some embodiments, any of the previous steps does not comprise performing an isolation step of a cell population comprising CD4/CD8 double-positive cells.

In some embodiments, the pluripotent stem cell is an induced pluripotent stem cell (iPSC).

In some aspects, a method of producing CD56+/CD3− immune cells is provided, said method comprising the step of (II) culturing cells comprising hematopoietic progenitor cells (HPC) (HP cell bulk) in a culture medium to produce CD56+/CD3− immune cells.

In some embodiments, the step (II) comprises: (X) culturing cells comprising hematopoietic progenitor cells (HPC) in a culture medium to produce CD4/CD8 double-positive cells; and (Y) culturing the cells obtained in step (X) in a culture medium to produce CD56+/CD3− immune cells.

In some embodiments, the step (II) does not comprise performing an isolation step of CD4/CD8 double positive cells.

In some embodiments, step (A) comprises a culture medium having at least one compound selected from bone morphogenetic protein-4 (BMP4) vascular endothelial growth factor (VEGF), basic fibroblast growth factor (bFGF), ascorbic acid, Flt3 ligand (Flt3L), thrombopoietin (TPO) and TGFβ inhibitor.

In some embodiments, step (a) or step (X) comprises a culture medium having at least one compound selected from the group consisting of ascorbic acid, stem cell factor (SCF), IL-7, Flt3L, thrombopoietin (TPO), p38 inhibitor and SDF-1.

In some embodiments, step (b) or step (Y) comprises a culture medium having at least one compound selected from the group consisting of a CD3 activator, IL-2 and IL7.

In some embodiments, method further comprising culturing cells produced after step (b) or step (Y) in a culture medium comprising IL-7 and/or IL-15.

In some embodiments, culturing is performed at about 5% oxygen.

In some embodiments, step (A) lasts for about 10 days. In another embodiment, step (A) lasts for about 10-18 days.

In some embodiments, the iPSC are produced from peripheral blood mononuclear cells.

In some embodiments, at least about 50%, 55%, 60%, 75%, 80%, 85% or 90% of produced cells are CD56+/CD3− cells.

In some embodiments, less than about 25% of cells produced are CD3+ cells.

In some embodiments, the method further comprising a step of isolating CD56+/CD3− cells.

In some embodiments, CD56+/CD3− cells are isolated by fluorescence-activated cell sorting (FACS).

In some embodiments, the CD56+ immune cells are CD56+/CD3−.

In some embodiments, any pluripotent, multipotent, or patient-derived HPC can be used with the methods described herein. For example, in some embodiments, the cell is an embryonic stem cell. In some embodiments, the cell is an adult stem cell. Various adult stem cells are known in the art, and include for example, mesenchymal stem cells, hematopoietic stem cells, umbilical-cord derived cells, bone marrow stem cells, adipose stem cells and the like. In some embodiments, the cell is an induced-pluripotent stem cell (iPSC). Thus, the NK cells produced in accordance with the methods described herein can be made from any pluripotent, multipotent or patient-derived HPC, such as a primary HPC derived directly from a donor.

In some embodiments, the cells that are used to produce the NK cell described herein are genetically modified at any stage of cellular differentiation. In some embodiments, the cells used to produce the NK cell described herein are genetically modified at a pluripotent, multipotent or unipotent stage. For example, in some embodiments, the cells used to produce the NK cell described herein are genetically modified at a pluripotent stage. For example, the cell can be genetically modified at an embryonic stem cell stage or iPSC stem cell stage. In some embodiments, the cells used to produce the NK cell described herein are genetically modified at a multipotent stage. For example, the cell can be genetically modified at the HSC stage.

In some embodiments, wherein the cells are genetically modified to express one or more chimeric antigen receptors (CAR).

In some embodiments, the isolated CD56+/CD3− cells are genetically modified to express one or more chimeric antigen receptors (CAR).

In some embodiments, the antigen is CD19.

In some embodiments, the cells are further genetically modified to express IL-15Rα/IL-15 complex.

In some aspects, an unsorted cell population is provided, the cell population comprising pluripotent stem cell-derived CD56+/CD3− cells at a ratio of not less than 60% of total pluripotent stem cell-derived CD56+ immune cells.

In some embodiments, less than 25% of cells are CD3+ cells.

In some embodiments, less than 5% of cells are monocytes.

In some embodiments, less than 5% of cells are B cells.

In some aspects, a method of treating a subject in need of cell therapy is provided, the method comprising administering to the subject pluripotent stem cell-derived CD56+/CD3− immune cells of any one of the preceding claims.

In some embodiments, the subject has a cancer.

In some embodiments, the cancer is leukemia or lymphoma.

Various culture media are used in the methods described herein, including, for example HPC induction media, CD4/CD8 induction media, and NK induction media.

In some aspects, induced pluripotent cells (iPSCs) are cultured in HPC induction media for a period of time to generate a population of cells comprising hematopoietic progenitor cells, this population of cells is referred to herein as HP cell bulk. In some embodiments, this period of time is between about 10 and 14 days. In some embodiments, this period of time is for about 13 days. In some embodiments, the HPC induction media comprises one or more of BMP4, VEGF, bFGF, ascorbic acid, a TGFβ inhibitor, stem cell factor (SCF), thrombopoietin TPO, and Flt3L. In some embodiments, the iPSCs are cultured from day 1 to about day 10 in HPC induction media comprising VEGF, bFGF, ascorbic acid. In some embodiments, VEGF is at a concentration of about 50 ng/mL. In some embodiments, the bFGF is at a concentration of about 50 ng/mL. In some embodiments, the ascorbic acid is at a concentration of about 50 μg/mL. In some embodiments, the iPSCs are cultured from day 1 to about day 3 in HPC induction media comprising BMP4. In some embodiments, the BMP4 is at a concentration of about 50 ng/mL. In some embodiments, iPSCs are cultured from about day 2 to about day 3 with a TGFβ inhibitor, such as SB431542 at a concentration of about 6 μM. In some embodiments, between days 7-13 of the culture one or more of stem cell factor (SCF), thrombopoietin TPO, and Flt3L are added to the culture. In some embodiments, SCF is added at a concentration of about 50 ng/mL. In some embodiments, TPO is added at a concentration of about 30 ng/ml. In some embodiments, Flt3L is added at a concentration of about 10 ng/ml.

In some aspects, the HP cell bulk population is cultured in CD4/CD8 induction media for a period of time to generate a population of cells comprising an intermediate heterogeneous cell population comprising CD4−/CD8− cells, CD4−/CD8+ cells, CD4+/CD8−, and CD4+/CD8+ cells. In some embodiments, the HP cell bulk population is cultured in CD4/CD8 induction media for between 19-22 days. In some embodiments, the HP cell bulk population is cultured in CD4/CD8 induction media for about 21 days. In some embodiments, the CD4/CD8 induction media comprises one or more of ascorbic acid, SCF, TPO, Flt3L, IL7, a p38MAPKi inhibitor such as SB203580, SDF1a. In some embodiments, the ascorbic acid is at a concentration of about 50 μg. In some embodiments, the SCF is at a concentration of 50 ng/mL. In some embodiments, the TPO is at a concentration of about 100 ng/mL. In some embodiments, the Flt3L is at a concentration of about 50 ng/mL. In some embodiments, the IL7 is at a concentration of about 50 ng/mL. In some embodiments, the SB203580 is at a concentration of about 15 μM. In some embodiments, the SDF1a is at a concentration of about 30 nM. In some embodiments, the HP cell bulk is cultured on a culture dish coated with hDLL4/RetroNectin.

In some embodiments, the CD4/CD8 induction medium comprises at least one compound selected from the group consisting of ascorbic acid, stem cell factor (SCF), IL-7, Flt3L, thrombopoietin (TPO), p38 inhibitor and SDF-1. In some embodiments, the CD4/CD8 induction medium comprises a p38 inhibitor. In some embodiments, the CD4/CD8 induction medium comprises SDF-1. In some embodiments, the CD4/CD8 induction medium comprises an p38 inhibitor and SDF-1.

In some aspects, the heterogeneous cell population comprising CD4−/CD8− cells, CD4−/CD8+ cells, CD4+/CD8−, and CD4+/CD8+ cells is cultured in NK induction media for a period of time to generate a population of cells comprising CD56+/CD3− NK cells. In some embodiments, the heterogeneous cell population is cultured for a period of between about 5-9 days in NK induction media. In some embodiments, the cell population is cultured for about 7 days. In some embodiments, the NK cell induction media comprises one or more of IL-7, IL-2 and anti-CD3 antibody. In some embodiments, the heterogeneous cell population is cultured about 7 days in NK cell induction media comprising IL-7 and IL-2. In some embodiments, the IL-7 is at a concentration of about 10 ng/mL. In some embodiments, the IL-2 is at a concentration of about 10 ng/mL. In some embodiments, the heterogeneous population is cultured in NK cell induction media comprising anti-CD3 for a period of about 3 days. In some embodiments, this method generates greater than 50%, 60%, 70%, 80%, 90%, or 95% CD56+/CD3− cells. Accordingly, in some embodiments, this method generates greater than 50% CD56+/CD3− cells. In some embodiments, this method generates greater than 60% CD56+/CD3− cells. In some embodiments, this method generates greater than 70% CD56+/CD3− cells. In some embodiments, this method generates greater than 80% CD56+/CD3− cells. In some embodiments, this method generates greater than 90% CD56+/CD3− cells. In some embodiments, this method generates greater than 95% CD56+/CD3− cells.

DEFINITIONS

Figure 1:
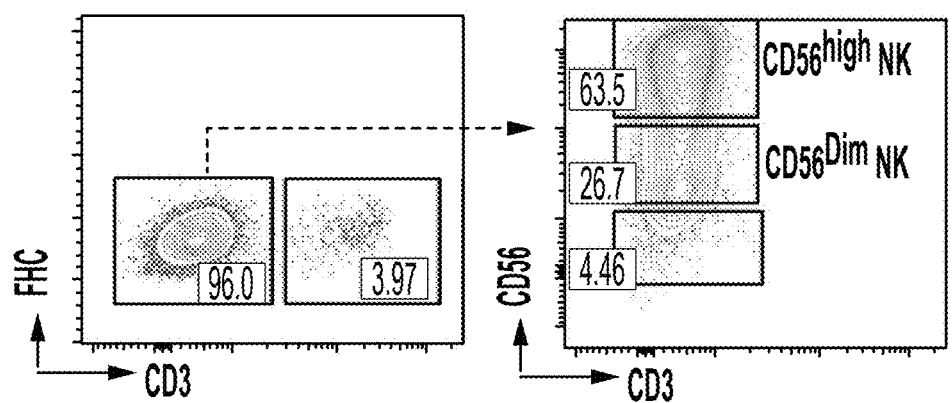
FIG. 1 is a series of flow cytometry plots that show the results of flow cytometry analysis of a NK cell bulk population that was obtained using the methods described herein. Briefly, iPS cells were cultured as described herein, without an intermediate isolation step. The flow cytometry graphs show the presence of a population of CD3 negative cells that are CD56$^{high}$ (approximately 63.5% of the NK cell bulk population) and a population of CD3 negative cells that are CD56$^{dim}$ (approximately 26.7% of the NK cell bulk population). Both of these populations are NK cells. Thus, the total CD56 positive, CD3 negative NK cell population obtained is greater than 90% of the total cell population.

Administering: As used herein, the terms "administer," "administering," "administration" "introducing" or "introduction" are used interchangeably in the context of delivering therapeutic cells, for example, iPSC or HPC derived CD56+/CD3− immune cells, into a subject, by a method or route which results in delivery of such cells. Various methods are known in the art for administering cells, including for example intravenously, topically, orally, intramuscularly, intraperitoneally, intrathecally, subcutaneously or transdermally. Cells can be administered with or without a carrier.

Adoptive Cell Therapy: As used herein interchangeably, the terms "adoptive cell therapy" or "adoptive cell transfer" or "cell therapy" or "ACT" refer to the transfer of cells, for example, a population of CD56+/CD3− cells generated using methods described herein and administered into a subject or patient in need thereof. In some embodiments, the cell is a CD56+/CD3− immune cell made using a method described herein and additionally expressing a CAR.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Antigen-Specific Targeting Domain: "antigen-specific targeting domain" provides the CAR with the ability to bind to a target antigen of interest. In some embodiments, the antigen-specific targeting domain targets an antigen of clinical interest against which it would be desirable to trigger an effector immune response that results in tumor killing. The antigen-specific targeting domain may be any protein or peptide that possesses the ability to specifically recognize and bind to a biological molecule (e.g., a cell surface receptor or tumor protein, or a component thereof). The antigen-specific targeting domain includes any naturally occurring, synthetic, semi-synthetic, or recombinantly produced binding partner for a biological molecule of interest.

Illustrative antigen-specific targeting domains include, for example, antibodies or antibody fragments or derivatives, extracellular domains of receptors, ligands for cell surface molecules/receptors, or receptor binding domains thereof, and tumor binding proteins.

In some embodiments, the antigen-specific targeting domain is, or is derived from, an antibody. An antibody-derived targeting domain can be a fragment of an antibody or a genetically engineered product of one or more fragments of the antibody, which fragment is involved in binding with the antigen. Examples include a variable region (Fv), a complementarity determining region (CDR), a Fab, a single chain antibody (scFv), a heavy chain variable region (VH), a light chain variable region (VL) and a camelid antibody (VHH).

In some embodiments, the binding domain is a single chain antibody (scFv). The scFv may be murine, human or humanized scFv.

Allogeneic: "Allogeneic" as used herein, refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently different genetically to interact antigenically.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). It is understood that when the term "about" or "approximately" is used to modify a stated reference value, the stated reference value itself is covered along with values that are near the stated reference value on either side of the stated reference value.

Ascorbic Acid or Vitamin C: As used herein, "ascorbic acid" or "vitamin C" means L-ascorbic acid and derivatives thereof, and "L-ascorbic acid derivative" means derivatives that become vitamin C by enzymatic reaction in the living body. Examples of the derivatives of L-ascorbic acid include vitamin C phosphate, ascorbic acid glucoside, ascorbyl ethyl, vitamin C ester, ascorbyl tetrahexyldecanoate, ascorbyl stearate, and ascorbyl 2-phosphate 6-palmitate. Examples of the vitamin C phosphate include salts of L-ascorbic acid phosphate such as L-ascorbic acid phosphate Na and L-ascorbic acid phosphate Mg. In one embodiment, the vitamin C can be ascorbic acid 2-phosphate.

Bulk cell population: The term "bulk cell population," "bulk cell" and the like refers to a heterogeneous population of cells. In some embodiments, the bulk cell population comprises hematopoietic cells. In some embodiments, the bulk cell population may be obtained from pluripotent cells, e.g., induced pluripotent stem cells. In some embodiments, the bulk cell population is obtained from donor tissue, including, for example, blood.

CD4/CD8 induction media: The term CD4/CD8 induction media as used herein refers to cell culture media that is used to obtain a population of cells that comprises CD4−/CD8− cells, CD4+/CD8+ cells, CD4+/CD8− cells, CD4−/CD8+ cells. In some embodiments, the CD4/CD8 induction media is used to differentiate HP cell bulk to a population of cells that comprise CD4−/CD8− cells, CD4+/CD8+ cells, CD4+/CD8− cells, CD4−/CD8+ cells. In some embodiments, the CD4/CD8 induction media comprises one or more, or all, of ascorbic acid, SCF. TPO, Flt3L, IL7, a p38MAPKi inhibitor such as SB203580, and SDF1a.

Chimeric Antigen Receptor (CAR): As used herein, the term "chimeric antigen receptor" or "CAR" engineered receptors which can confer an antigen specificity onto cells (for example NK cells, T cells such as naive T cells, central memory T cells, effector memory T cells or combinations thereof). CARs are also known as artificial T-cell receptors, chimeric T-cell receptors or chimeric immunoreceptors. In some embodiments, the CARs of the invention comprise an antigen-specific targeting domain, an extracellular domain, a transmembrane domain, optionally one or more co-stimulatory domains, and an intracellular signaling domain. In some embodiments described herein, a CAR is introduced into CD56+/CD3− immune cells (e.g., NK or NK-like cells) made using a method described herein, such that to redirect specificity for a desired cell-surface antigen or MHC-peptide complex. These synthetic receptors typically contain a target binding domain that is associated with one or more signaling domains via a flexible linker in a single fusion molecule. The target binding domain is used to direct the immune cell (e.g., a CD56+/CD3+ immune cell) to specific targets on the surface of pathologic cells (e.g., a cancer cell) and the signaling domains contain molecular machinery for immune cell (e.g., CD56+/CD3− immune cell) activation and proliferation. The flexible linker which usually passes through the immune cell (e.g., CD56+/CD3− cell) membrane (i.e., forming a transmembrane domain) allows for cell membrane display of the target binding domain of the CAR. CARs have successfully allowed immune cells to be redirected against antigens expressed at the surface of tumor cells from various malignancies including lymphomas and solid tumors (Gross et al., (1989) Transplant Proc., 21 (1 Pt 1): 127-30; Jena et al., (2010) Blood, 116 (7): 1035-44). A CAR's extracellular binding domain may be composed of a single chain variable fragment (scFv) derived from fusing the variable heavy and light regions of a murine or humanized monoclonal antibody. In some embodiments, the extracellular binding domain comprises a single domain antibody. Alternatively, scFvs may be used that are derived from Fab's (instead of from an antibody, e.g., obtained from Fab libraries). In various embodiments, this scFv is fused to a transmembrane domain and then to an intracellular signaling domain. At least three generations of CARs have been developed. The first generation CARs comprised target binding domains attached to a signaling domain derived from the cytoplasmic region of the CD3zeta or the Fc receptor gamma chains. First generation CARs were shown to successfully redirect immune cells to the selected target, but they failed to provide prolonged expansion and antitumor activity in vivo. Second and third generation CARs have focused on enhancing modified cell survival and increasing proliferation by including co-stimulatory molecules, such as CD28, OX-40 (CD134) and 4-1BB (CD137).

Culture: The term "culture" or "cell culture" or "culturing" refers to the maintenance, growth and/or differentiation of cells in an in vitro environment. In various methods described herein, cells are cultured in a particular cell culture medium (or "media" in case of a plural) which facilitates or promotes the growth or differentiation of one type of cell into a different type of cell. For example, in certain embodiments described herein, culturing iPSCs in a cell culture medium results in at least 20%, 30%, 40%, 50%, 60%, 70%, or 80% of cells becoming CD34+ cells (i.e., HPCs) in the total cell population. In some embodiments described herein, culturing a cell population containing at least 20%, 30%, 40%, 50%, 60%, 70%, or 80% 30% HPCs results in a cell population comprising CD4−/CD8− cells, CD4−/CD8+ cells, CD4+/CD8−, and CD4+/CD8+ cells. In yet other embodiments, culturing a cell population of cells containing CD4−/CD8− cells, CD4−/CD8+ cells, CD4+/CD8−, and CD4+/CD8+ cells results in an enriched CD56+/CD3− cell population (i.e., at least 50% of cells in the total cell population are CD56+/CD3−). A cell culture medium acts as a source of nutrients, hormones and/or other factors helpful to propagate and/or sustain the cells.

Differentiating: The terms "differentiating." "inducing." "converting." "deriving" and the like refer to process in which a cell of one phenotype undergoes a change to a cell of another phenotype.

Engineered: The term "engineered", as used herein, describes a polynucleotide, polypeptide or a cell that has been designed or modified and/or whose existence and production require intervention and/or activity. For example, an engineered cell that is intentionally designed to elicit a particular effect and that differs from the effect of naturally occurring cells of the same type. In some embodiments, an engineered cell is a CD56+/CD3− cell derived from iPSCs or HPCs using a method described herein and further expresses a chimeric antigen receptor.

Enriched: The term "enriched" as used herein in reference to a specific cell type means a cell population that has at least 20%, 25%, 30%, 35%, 40%, 45%, 50%, 55%, 60%, 65%, 70%, 75%, 80%, 85%, or 90% of the specific cell type within the cell population as determined by flow cytometry or other analytical method.

Ex vivo: As used herein, the term "ex vivo" means a process in which cells are removed from a living organism and are propagated outside the organism (e.g., in a test tube, in a culture bag, in a bioreactor).

Functional equivalent or derivative: As used herein, the term "functional equivalent" or "functional derivative" denotes, in the context of a functional derivative of an amino acid sequence, a molecule that retains a biological activity (either function or structural) that is substantially similar to that of the original sequence. A functional derivative or equivalent may be a natural derivative or is prepared synthetically. Exemplary functional derivatives include amino acid sequences having substitutions, deletions, or additions of one or more amino acids, provided that the biological activity of the protein is conserved. The substituting amino acid desirably has chemico-physical properties which are similar to that of the substituted amino acid. Desirable similar chemico-physical properties include, similarities in charge, bulkiness, hydrophobicity, hydrophilicity, and the like.

Hematopoietic progenitor cell: The term "hematopoietic progenitor cell" or "hematopoietic progenitor cells" or "HPC" or "HPCs" refers to CD34+ cells which are committed to a hematopoietic lineage but are capable of further hematopoietic differentiation and include hematopoietic stem cells, multipotential hematopoietic stem cells, common myeloid progenitors, megakaryocyte progenitors, erythrocyte progenitors, and lymphoid progenitors.

HPC bulk: The terms "HPC bulk." "Hematopoietic progenitor cell bulk," or "HP cell bulk" mean a heterogenous population of cells comprising hematopoietic progenitor cells. In some embodiments, the HPC bulk is derived from iPSCs. In some embodiments, the HPC bulk is derived from blood.

HPC derived NK cells: The term "HPC derived NK cells" means CD56+/CD3− immune cells (e.g., NK or NK-like cells) that are obtained from an HPC bulk population following culture in a cell culture medium.

HPC induction media: The term HPC induction media as used herein refers to culture media that is used generate a population of cells comprising hematopoietic cells from a starting cell population. In some embodiments, the starting cell population is iPSCs. In some embodiments, the HPC induction media comprises one or more of BMP4, VEGF, bFGF, ascorbic acid, a TGFβ inhibitor, stem cell factor (SCF), thrombopoietin TPO, and Flt3L.

Immune cells: As used herein, the term "immune cell" or "immune cells" refers to cells of the immune system, including, but not limited to, T cells, NK cells, T/NK cells, dendritic cells, macrophages, B cells, neutrophils, erythrocytes, monocytes, basophils, neutrophils, mast cells, eosinphils, and any combination thereof. In various embodiments, the immune cells produced using methods described herein are NK cells, characterized as CD56+/CD3− cells.

Induced Pluripotent Stem Cell (iPSC): As used herein, the term "induced pluripotent stem cell" or "iPSC" refers to refers to a pluripotent stem cell artificially derived (e.g., induced) from a non-pluripotent cell, typically an adult somatic cell, for example, by inducing expression of one or more genes (including POU4F1/OCT4 (Gene ID; 5460) in combination with, but not restricted to, SOX2 (Gene ID; 6657), KLF4 (Gene ID; 9314), cMYC (Gene ID; 4609), NANOG (Gene ID; 79923), LIN28/LIN28A (Gene ID; 79727)). The stem cells may be genetically modified at any stage with markers or gene so that the markers or genes are carried through to any stage of culturing. The markers may be used to purify or enrich the differentiated or undifferentiated stem cell populations at any stage of culture.

Induction medium: The term "induction medium" generally refers to a cell culture media that is used to differentiate a population of cells from a first cell phenotype to a second cell phenotype. In some embodiments, the first cell phenotype and the second cell phenotypes comprise a heterogeneous population of cells. In some embodiments, the first cell phenotype comprises a heterogeneous population of cells. In some embodiments, the second cell phenotype comprises a heterogeneous population of cells. In some embodiments, the induction medium is used to differentiate a population of heterogeneous cells to a population of cells that is substantially homogeneous.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolation step: The term "isolation step." or "cell isolation step" as used herein, means a step of separating particular cell type from a mixture of cells. Various methods of separating particular cell types from a mixture of cells are known in the art, and include, for example fluorescence-activated cell sorting (FACS) and magnetic-bead based sorting strategies such as magnetic-activated cell sorting (MACS).

Natural Killer (NK) Cell: As used herein, "natural killer cell" or NK cell is a lymphoid cell defined by its marker expression and function/activity. For example, in humans an NK cell expresses CD56. In a further embodiment, such NK cells may express CD56 and CD16. In another example, such NK cells may be CD56+/CD3− cells. NK cells may express variable levels of CD56. For example, NK cells may be "CD56$^{high}$" which means that the NK cells express a high level of CD56 as assessed by methods in the art, for example as assessed by flow cytometry. As another example, NK cells may be "CD56$^{dim}$" which means that the NK cells express a low but detectable level of CD56 as assessed by methods in the art, for example as assessed by flow cytometry.

NK induction media: In some embodiments, the term "NK induction media" refers to a cell culture media that is used to generate a population of cells comprising CD56+/CD3− cells. In some embodiments, the NK cell induction media comprises one or more of IL-7, IL-2 and anti-CD3 antibody.

iPS NK Cell: As used herein, "iPS NK cells" are iPSC derived NK Cells, for example, NK cells that are derived from iPSCs as starting materials. Such iPS NK cell expresses CD56. In a further embodiment, such iPS NK cells may express CD56 and CD16. In another example, such iPS NK cells may express CD56 and be CD3− (CD56+/CD3−). iPS NK cells are also referred to herein as "iNK cells".

T cell: As used herein "T cell" is a lymphoid cell defined by its marker expression and function/activity. For example, in humans a T cell expresses CD3. CD56+/CD3+ cells are known as NKT cell.

Single-chain Fv antibody" or "scFv" refers to an engineered antibody that includes a light chain variable region and a heavy chain variable region connected to one another directly or via a peptide linker sequence.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Suffering from: An individual who is "suffering from" a disease, disorder, and/or condition has been diagnosed with or displays one or more symptoms of the disease, disorder, and/or condition. The disease may include cancer, for example, lymphoma and leukemia.

Therapeutically effective amount: As used herein, the term "therapeutically effective amount" of a therapeutic agent (e.g., a cell therapy) means an amount (e.g., a certain number of cells or a cell population enriched with a certain percentage of a particular type or types of cell or cells) that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose. In some embodiments, the CD56+/CD3− cells described herein are modified to express one or more transgenes. In some embodiments, the CD56+/CD3− cells described herein are modified to express a chimeric antigen receptor, such as for example CD19. In some embodiments, between about 100 million and 900 million CD56+/CD3− cells described herein are administered to a subject in need thereof. In some embodiments, between about 100 million and 700 million CD56+/CD3− cells described herein are administered to a subject in need thereof. In some embodiments, between about 100 million and 500 million CD56+/CD3− cells described herein are administered to a subject in need thereof. In some embodiments, between about 200 million and 900 million CD56+/CD3− cells described herein are administered to a subject in need thereof. In some embodiments, between about 200 million and 700 million CD56+/CD3− cells described herein are administered to a subject in need thereof. In some embodiments, between about 200 million and 500 million CD56+/CD3− cells described herein are administered to a subject in need thereof.

Treating: As used herein, the term "treat," "treatment." or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

The recitation of numerical ranges by endpoints herein includes all numbers and fractions subsumed within that range (e.g. 1 to 5 includes 1, 1.5, 2, 2.75, 3, 3.9, 4 and 5). It is also to be understood that all numbers and fractions thereof are presumed to be modified by the term "about."

Various aspects of the invention are described in detail in the following sections. The use of sections is not meant to limit the invention. Each section can apply to any aspect of the invention. In this application, the use of "or" means "and/or" unless stated otherwise. As used herein, the singular forms "a", "an", and "the" include both singular and plural referents unless the context clearly dictates otherwise.

Various aspects of the invention are described in detail in the following sections. The use of sections is not meant to limit the invention. Each section can apply to any aspect of the invention. In this application, the use of "or" means "and/or" unless stated otherwise.

DETAILED DESCRIPTION

The present disclosure provides methods of producing NK cells from a pluripotent cell, such as an iPS cell or hematopoietic progenitor cell (HPC). The NK cells produced from iPSC are referred to herein as iPS derived NK cells, iPS NK cells or iNK cells. The disclosure provides cell culturing methods in which progenitor cells such as iPSC or HPC can be differentiated with high efficiency to NK cells or iPS NK cells without the need for an isolation step. The disclosure also shows that the obtained iPS NK cells are functional, and can be further genetically modified, for example through the introduction of a chimeric antigen receptor (CAR), useful for the treatment of various diseases or disorders, such as cancer.

Various methods of producing CD56+/CD3− cells (NK cells) are described below in more detail.

Method of Producing NK or iPS Derived NK Cells from Pluripotent Cells without an Isolation Step In some embodiments, a method of producing NK cells or iPS derived NK cells is provided, which method does not require an isolation step.

Overview of Culture Method

The methods provided herein allow for the production of CD56+/CD3− cells without any intervening isolation steps. In some embodiments, the methods comprise culturing a pluripotent stem cell, such as an iPSC, in HPC induction media to obtain a population of cells comprising hematopoietic cells (HPC) (HP cell bulk). The HP cell bulk population is subsequently cultured without performing an isolation step in CD4/CD8 induction media to obtain a cell population comprising CD4/CD8 double-positive cells. In some embodiments, the cell population comprising CD4/CD8 double-positive cells also comprises CD4+/CD8− cells, CD4−/CD8− cells, and CD4−/CD8+ cells. This is followed by a subsequent culturing period without performing an isolation step in which the cells are cultured in NK induction media to obtain a population enriched in CD56+/CD3− immune cells. Accordingly, in some embodiments, the method of producing CD56+/CD3− cells comprises: 1) culturing a pluripotent cell in HPC induction media to obtain a population comprising hematopoietic cells (HP cell bulk); 2) culturing the HP cell bulk in a CD4/CD8 induction media to obtain a population of cells that comprise CD4+/CD8− cells, CD4−/CD8− cells, and CD4−/CD8+ cells; and 3) culturing the population of cells that comprise CD4+/CD8− cells, CD4−/CD8− cells, and CD4−/CD8+ cells in NK induction for a period of time to obtain CD56+/CD3− cells.

In some embodiments, a method of producing NK cells or iPS NK cells comprises culturing cells comprising hematopoietic progenitor cells (e.g., HP cell bulk) to produce a cell population comprising CD4/CD8 double-positive cells, followed by a subsequent culturing period without performing an isolation step in which the cell population is cultured in a medium to obtain a population enriched in CD56+/CD3− immune cells. In some embodiments, a method of producing pluripotent stem cell-derived CD56+/CD3− immune cells comprises culturing the pluripotent stem cells in one or more media. In some embodiments, a method of producing CD56+/CD3− immune cells comprises culturing a hematopoietic progenitor cells in one or more culture media. In some embodiments, a method of producing CD56+/CD3− immune cells comprises culturing a mixture or population of cells comprising CD4/CD8 double-positive cells in one or more culture media. In some embodiments, the population enriched in CD56+/CD3− immune cells can subsequently be separated by any suitable method known in the art, for example such as by FACS sorting, or magnetic bead-based isolation techniques. In one embodiment, iPS cells can be differentiated to iPS NK cell in about 4-8 weeks, 5-7 weeks, or around 6 weeks. Accordingly, in some embodiments, the iPS cells can be differentiated to NK cells in about 4-8 weeks. In some embodiments, the iPS cells can be differentiated to NK cells in about 5-7 weeks. In some embodiments, the IPS cells can be differentiated to NK cells in about 6 weeks.

The cell differentiation process can be assessed by various means known in the art. For example, in some embodiments, the cell differentiation of cultured cells can be assessed by obtaining a sample of the cultured cells and subjecting that sample of cultured cells to one or more analytical methods to ascertain the cell phenotype of the cell. Known methods of ascertaining cell phenotype include for example, flow cytometry and immunofluorescence imaging. Any suitable sampling and phenotyping assay can be used with cell culture methods described herein to ascertain the progress of the cell differentiation process. In some embodiments, the methods described herein include one or more sampling steps to determine cell phenotype at a given time.

Overview of iPSC to HP Cell Bulk

In some embodiments, a pluripotent cell, such as an iPSC is cultured in HPC induction media to produce a population comprising HP cell bulk. In some embodiments, culturing of iPSC in HPC induction media to obtain HPC cell bulk comprises culturing the iPSC in the HPC induction media. The HPC induction media can comprise various components which allow for the production of HP cell bulk. In some embodiments, the HPC induction media comprises at least one or more compounds selected from bone morphogenetic protein-4 (BMP4), vascular endothelial growth factor (VEGF), basic fibroblast growth factor (bFGF), ascorbic acid, ROCK inhibitor, GSK3 inhibitor, stem cell factor (SCF), thrombopoietin (TPO), Flt3L, and TGFβ inhibitor. Accordingly, in some embodiments, the HPC induction media to induce HPC from iPSC comprises BMP4. In some embodiments, the culture medium to induce HPC from iPSC comprises VEGF. In some embodiments, the culture medium to induce HPC from iPSC comprises bFGF. In some embodiments, the culture medium to induce HPC from iPSC comprises TGFβ.

The iPSC are cultured in the HPC induction media period for a period of time sufficient to produce HP cell bulk. In some embodiments, the iPSC are cultured in HPC induction media for a period of between about 7-21 days, or 10-18 days, or around 14 days. In some embodiments, the iPSC are cultured in HPC induction media for a period of about 13 days.

In some embodiments, the cells are cultured in low-oxygen conditions such as, for example, about 3%, 4%, 5%, or 6% $O_2$. Accordingly, in some embodiments, the cells are cultured in about 3% $O_2$. In some embodiments, the cells are cultured in about 4% $O_2$. In some embodiments, the cells are cultured in about 5% O2. In some embodiments, the cells are cultured in about 6% $O_2$.

Overview of HP Cell Bulk to CD4/CD8

In some embodiments, the HPC cell bulk, or HPC obtained otherwise, e.g., a primary HPC isolated from a human donor or HPC differentiated from other stem cell sources/types such as embryonic stem cell derived, are further cultured without any intervening isolation step in a medium to obtain a population of cells comprising CD4/CD8 double-positive (DP) cells. In some embodiments, the HPC cell bulk, or HPC obtained otherwise, e.g., a primary HPC isolated from a human donor or HPC differentiated from other stem cell sources/types such as embryonic stem cell derived, are further cultured without any intervening isolation step in a medium to obtain a cell population comprising CD4+/CD8 cells. In some embodiments, the HPC cell bulk, or HPC obtained otherwise, e.g., a primary HPC isolated from a human donor or HPC differentiated from other stem cell sources/types such as embryonic stem cell derived, are further cultured without any intervening isolation step in a medium to obtain a cell population comprising CD4−/CD8− cells. In some embodiments, the HPC cell bulk, or HPC obtained otherwise, e.g., a primary HPC isolated from a human donor or HPC differentiated from other stem cell sources/types such as embryonic stem cell derived, are further cultured without any intervening isolation step in a medium to obtain a cell population comprising CD4−/CD8+ cells. It should be understood that the cell population obtained by this method includes CD4−/CD8− cells, CD4−/CD8+ cells, CD4+/CD8+ cells and CD4+/CD8− cells. The cell population includes, for example, lymphocytes. In some embodiments, the HPC cell bulk are cultured in CD4/CD8 induction media having at least one compound selected from the group consisting of ascorbic acid, stem cell factor (SCF), IL-7, Flt3L, TPO, fibronectin or a variant thereof, Notch ligand (e.g., Jag-1, Jag-2, DLL-1, DLL-3, DLL-4), p38 inhibitor and SDF-1 to obtain a population comprising CD4−/CD8− cells, CD4−/CD8+ cells, CD4+/CD8+ cells and CD4+/CD8− cells. Accordingly, in some embodiments, HPC cell bulk are cultured in CD4/CD8 induction media comprising ascorbic acid to obtain a population comprising CD4−/CD8− cells, CD4−/CD8+ cells, CD4+/CD8+ cells and CD4+/CD8− cells. In some embodiments, the HPC cell bulk are cultured in CD4/CD8 induction media comprising SCF to obtain a population comprising CD4−/CD8− cells, CD4−/CD8+ cells, CD4+/CD8+ cells and CD4+/CD8− cells. In some embodiments, the HPC cell bulk are cultured in CD4/CD8 induction media comprising IL-7 to obtain a population comprising CD4−/CD8− cells, CD4−/CD8+ cells, CD4+/CD8+ cells and CD4+/CD8− cells. In some embodiments, the HPC cell bulk are cultured in CD4/CD8 induction media comprising Flt3L to obtain a population comprising CD4−/CD8− cells, CD4−/CD8+ cells, CD4+/CD8+ cells and CD4+/CD8− cells. In some embodiments, the HPC cell bulk are cultured in CD4/CD8 induction media comprising p38 inhibitor to obtain a population comprising CD4−/CD8− cells, CD4−/CD8+ cells, CD4+/CD8+ cells and CD4+/CD8− cells. In some embodiments, the HPC cell bulk are cultured in CD4/CD8 induction media comprising SDF-1 to obtain a population comprising CD4−/CD8− cells, CD4−/CD8+ cells, CD4+/CD8+ cells and CD4+/CD8− cells.

The culture period to for a time suitable to obtain a population of cells comprising CD4−/CD8− cells, CD4−/CD8+ cells, CD4+/CD8+ cells and CD4+/CD8− cells. In some embodiments, the culturing of HP cell bulk to obtain a population of cells comprising CD4−/CD8− cells, CD4−/CD8+ cells, CD4+/CD8+ cells and CD4+/CD8− cells is about 2-6 weeks; 3-5 weeks or around 3 weeks. Accordingly, in some embodiments, the cell culture period is for about 2-6 weeks. In some embodiments, the cell culture period is for about 3-5 weeks. In some embodiments, the cell culture period is for about 3 weeks.

In some embodiments, the cells are cultured in low-oxygen conditions such as, for example, about 3%, 4%, 5%, or 6% $O_2$. Accordingly, in some embodiments, the cells are cultured in low-oxygen conditions such as, for example, about 3% $O_2$. In some embodiments, the cells are cultured in low-oxygen conditions such as, for example, about 4% $O_2$. In some embodiments, the cells are cultured in low-oxygen conditions such as, for example, about 5% $O_2$. In some embodiments, the cells are cultured in low-oxygen conditions such as, for example, about 6% $O_2$.

Overview of CD4/CD8 Cells to CD56+/CD3− Cells

The population of cells comprising CD4−/CD8− cells, CD4−/CD8+ cells, CD4+/CD8+ cells and CD4+/CD8− as described above, can be further cultured in a cell culture medium to obtain a population of CD56+/CD3− cells. In some embodiments, the culture medium is NK induction medium. In some embodiments, the NK induction medium comprises one or more of IL-7, IL-2 and anti-CD3 antibody.

In some embodiments, the population of cells comprising CD4−/CD8− cells, CD4−/CD8+ cells, CD4+/CD8+ cells and CD4+/CD8− are further cultured, without an intervening isolation step, in a culture medium to obtain a population of cells enriched in CD56+/CD3− cells. Such CD56+ cells include, for example, natural killer (NK) cells. In some embodiments the population comprising CD4−/CD8− cells, CD4−/CD8+ cells, CD4+/CD8+ cells and CD4+/CD8− cells are cultured in a medium that includes a CD3 activator, IL-2 and/or IL-7. Accordingly, in some embodiments, the population comprising CD4−/CD8− cells, CD4−/CD8+ cells, CD4+/CD8+ cells and CD4+/CD8− cells are cultured in a medium that includes a CD3 activator. CD3 activators are known in the art and include, for example, antibody complexes that bind CD3 and/or CD28 surface ligands. CD3 activators include, for example, an anti-CD3 antibody or a fragment bonded thereto can be used. In some embodiments, when an anti-CD3 antibody is used, the anti-CD3 antibody can be a polyclonal antibody or a monoclonal antibody. In some embodiments, the anti-CD3 antibody is a polyclonal antibody. In some embodiments, the anti-CD3 antibody is a monoclonal antibody. The antibody may belong to any immunoglobulin class of IgG, IgA, IgM, IgD, IgE, or IgG. Various kinds of anti-CD3 antibody can be used, including, for example, an antibody produced from OKT3 clone or UCHT1 clone can be used. The concentration of anti-CD3 antibody in the medium is, for example, between 10 ng/ml-1000 ng/ml.

In some embodiments, the population comprising CD4−/CD8− cells, CD4−/CD8+ cells, CD4+/CD8+ cells and CD4+/CD8− cells are cultured in a medium that includes IL-2. In some embodiments, the population comprising CD4−/CD8− cells, CD4−/CD8+ cells, CD4+/CD8+ cells and CD4+/CD8− cells are cultured in a medium that includes IL-7. In some embodiments, the cells are cultured in low-oxygen conditions such as, for example, about 3%, 4%, 5%, or 6% 02. Accordingly, in some embodiments, the cells are cultured in about 3% $O_2$. In some embodiments, the cells are cultured in about 4% $O_2$. In some embodiments, the cells are cultured in about 5% $O_2$. In some embodiments, the cells are cultured in about 6% $O_2$.

The cell population comprising CD56+ cells can be further cultured in NK induction media to enrich the population of CD56+/CD3− cells. In some embodiments, the cell population comprising CD56+ cells are cultured in NK induction media comprising IL-7 and/or IL-15 to further enrich the CD56+ cells. Thus, in some embodiments, the cell population comprising CD56+ cells are cultured in NK induction media comprising IL-7. In some embodiments, the cell population comprising CD56+ cells are cultured in NK induction media comprising IL-15. In some embodiments, the cells are cultured in low-oxygen conditions such as, for example, about 3%, 4%, 5%, or 6% $O_2$. In some embodiments, the CD56+/CD3− cells produced are NK cells. The percentage of CD56+/CD3− NK cells produced is at least about 50%, 55%, 60%, 75%, 80%, 85%, 90%, 95% or more than 95% %. Accordingly, in some embodiments, the method results in at least about 50% CD56+/CD3− NK cells. In some embodiments, the method results in at least about 55% CD56+/CD3− NK cells. In some embodiments, the method results in at least about 60% CD56+/CD3− NK cells. In some embodiments, the method results in at least about 65% CD56+/CD3− NK cells. In some embodiments, the method results in at least about 70% CD56+/CD3− NK cells. In some embodiments, the method results in at least about 75% CD56+/CD3− NK cells. In some embodiments, the method results in at least about 80% CD56+/CD3− NK cells. In some embodiments, the method results in at least about 85% CD56+/CD3− NK cells. In some embodiments, the method results in at least about 90% CD56+/CD3− NK cells. In some embodiments, the method results in at least about 95% CD56+/CD3− NK cells. In some embodiments, the method results in more than 95% CD56+/CD3− NK cells.

In some embodiments, about 5%, 10, 15%, 20%, 25%, or about 30% of the cells produced by this culturing method are CD3+ T cells. In some embodiments, less than 5% of the cells produced are CD3+ T cells. In some embodiments, about 5% of the cells produced are CD3+ T cells. In some embodiments, about 10% of the cells produced are CD3+ T cells. In some embodiments, about 15% of the cells produced are CD3+ T cells. In some embodiments, about 20% of the cells produced are CD3+ T cells. In some embodiments, about 25% of the cells produced are CD3+ T cells. In some embodiments, about 30% of the cells produced are CD3+ T cells.

In some embodiments, the population enriched in CD56+/CD3− cells are isolated by methods known in the art. Such methods include, for example, flow cytometry (FACS)-based sorting methods and magnetic-based sorting methods (MACS).

In some embodiments, the culturing period to obtain CD56+/CD3− NK cells from a population comprising CD4−/CD8− cells, CD4−/CD8+ cells, CD4+/CD8+ cells and CD4+/CD8 cells is about 4, 5, 6, 7, 8, 9, 10, 11, 12, 13, 14, 15, 16, 17 or 18 days. In some embodiments, the culturing period is about 7 days.

In some embodiments, the enriched CD56+ cell population comprise NK cells. In some embodiments, the enriched CD56+ cells comprise CD3-cells. In some embodiments, the enriched CD56+ cells comprise CD3+ cells.

Suitable Pluripotent Cells for Differentiation to CD56+/CD3-Cells

In some embodiments, any pluripotent, multipotent, or patient-derived HPC can be used with the methods described herein. For example, in some embodiments, the cell is an embryonic stem cell. In some embodiments, the cell is an adult stem cell. Various adult stem cells are known in the art, and include for example, mesenchymal stem cells, hematopoietic stem cells, umbilical-cord derived cells, bone marrow stem cells, adipose stem cells and the like. In some embodiments, the cell is an induced-pluripotent stem cell (iPSC). Thus, the NK cells produced in accordance with the methods described herein can be made from any pluripotent, multipotent or patient-derived HPC, such as a primary HPC derived directly from a donor.

In some embodiments, the pluripotent cell includes, for example, embryonic stem (ES) cells, embryonic stem cells derived from a cloned embryo obtained by nuclear transfer (ntES cells), germline stem cells ("GS cells"), embryonic germ cells ("EG cells"), iPS cells, and pluripotent cells derived from cultured fibroblasts or bone marrow stem cells (Muse cells). In some embodiments, the iPS cells can be derived from peripheral blood mononuclear cells of healthy individuals. Methods for producing iPS cells are known in the art. These cells can be produced by introducing reprogramming factors into arbitrary somatic cells. Examples of the reprogramming factors herein include genes such as Oct3/4, Sox2, Sox1, Sox3, Sox15, Sox17, Kif 4, Klf2, c-Myc, N-Myc, L-Myc, Nanog, Lin28, Fbx15, ERas, ECAT15-2, Tel1, beta-catenin, Lin28b, Sall1, Sall4, Esrrb, Nr5a2, Tbx3, and Glis1, and gene products thereof. These reprogramming factors may be used individually, or two or more of these may be used in combination. Examples of the combination of the reprogramming factors include those described in WO2007/069666, WO2008/118820, WO2009/007852, WO2009/032194, WO2009/058413, WO2009/057831, WO2009/075119, WO2009/079007, WO2009/091659, WO2009/101084, WO2009/101407, WO2009/

102983, WO2009/114949, WO2009/117439, WO2009/126250, WO2009/126251, WO2009/126655, WO2009/157593, WO2010/009015, WO2010/033906, WO2010/033920, WO2010/042800, WO2010/050626, WO2010/056831, WO2010/068955, WO2010/098419, WO2010/102267, WO2010/111409, WO2010/111422, WO2010/115050, WO2010/124290, WO2010/147395, WO2010/147612, Huangfu D, et al. (2008), Nat. Biotechnol., 26:795-797, Shi Y, et al. (2008), Cell Stem Cell, 2:525-528, Eminli S, et al. (2008), Stem Cells. 26:2467-2474, Eluangfu D, et al. (2008), Nat. Biotechnol. 26:1269-1275, Shi Y, et al. (2008), Cell Stem Cell, 3, 568-574, Zhao Y, et al. (2008), Cell Stem Cell, 3:475-479. Marson A. (2008), Cell Stem Cell, 3, 132-135, Feng B, et al. (2009), Nat. Cell Biol. 11:197-203, R. L. Judson et al., (2009), Nat. Biotechnol., 27:459-461, Lyssiotis C A, et al. (2009), Proc Natl Acad Sci USA. 106:8912-8917, Kim J, et al. (2009), Nature. 461:649-643, Ichida J K, et al. (2009), Cell Stem Cell. 5:491-503, Heng J C, et al. (2010), Cell Stem Cell. 6:167-74, Han J, et al. (2010), Nature. 463:1096-100, *Mali* P, et al. (2010), Stem Cells. 28:713-720, and Mackawa M, et al. (2011), Nature. 474:225-9.

The iPSC can be obtained from any suitable tissue. In some embodiments, the iPSC are obtained from peripheral blood mononuclear cells.

Hematopoietic progenitor cells (HPC) are cells that are capable of differentiation into blood cells such as lymphocytes, eosinophils, neutrophils, basophils, erythrocytes, and megakaryocytes. Hematopoietic progenitor cells or hematopoietic stem cells can be identified based on, for example, the presence of CD34 and/or CD43 surface antigens.

In some embodiments, the cells that are used to produce the CD56+/CD3– NK cells described herein are genetically modified at any stage of cellular differentiation. In some embodiments, the CD56+/CD3– NK cells are genetically modified to include a desired chimeric antigen receptor (CAR), T-cell receptor (TCR) or other engineered protein.

In some embodiments, the cells used to produce the CD56+/CD3– NK cell described herein are genetically modified at a pluripotent, multipotent or unipotent stage. For example, in some embodiments, the cells used to produce the CD56+/CD3– NK cell described herein are genetically modified at a pluripotent stage. For example, the cell can be genetically modified at an embryonic stem cell stage or iPSC stem cell stage. In some embodiments, the cells used to produce the CD56+/CD3– NK cell described herein are genetically modified at a multipotent stage. For example, the cell can be genetically modified at the hematopoietic stem cell (HSC) stage.

Culture Conditions—iPSC to HPC Cell Bulk

In some embodiments, the medium for the production of the hematopoietic progenitor cells (i.e., HPC induction media) from iPSC may be prepared by adding vitamin C to a basal medium which is used for culture of animal cells. Examples of the basal medium include Iscove's Modified Dulbecco's Medium (IMDM), Medium 199, Eagle's Minimum Essential Medium (EMEM), αMEM medium, Dulbecco's modified Eagle's Medium (DMEM), Ham's F12 medium, RPMI 1640 medium, Fischer's medium, and Neurobasal Medium (Life Technologies), and mixtures of two or more of these media. In some embodiments, medium contains serum. In some embodiments, the medium is serum-free.

In some embodiments, the HPC induction media may include StemPro™-34. StemPro™-34 is a serum-free medium that is formulated to support the development of human hematopoietic cells in culture.

If necessary, in some embodiments, the HPC induction media may also contain one or more substances such as albumin, human insulin, human transferrin, selenium or sodium selenite, fatty acid, trace elements, 2-mercaptoethanol, thiol glycerol, α-monothioglycerol, lipids, amino acids, L-glutamine, non-essential amino acids, vitamins, growth factors, low molecular weight compounds, antibiotics, antioxidants, pyruvic acid, buffers, inorganic salts, and cytokines.

In some embodiments, the HPC induction media includes IMDM medium containing serum, insulin, transferrin, selenium, thiol glycerol or α-monothioglycerol, L-glutamine, and ascorbic acid.

In some embodiments, the HPC induction media contains one or more substances that cause signal transduction of bone morphogenetic protein 4 (BMP4) signaling pathway. Such substances include, but not limited to, BMP4.

In some embodiments, the HPC induction media contains one or more substances that cause signal transduction of vascular epithelial growth factor (VEGF) signaling pathway. Such substances include, but not limited to, VEGF.

In some embodiments, the HPC induction media contains one or more substances that cause signal transduction of fibroblast growth factor (FGF) pathway. Such substances include, but not limited to, bFGF and FGF2.

In some embodiments, the HPC induction media contains one or more substances that cause signal transduction of stem cell factor/kit signaling pathway. Such substances include, but not limited to, SCF.

In some embodiments, the HPC induction media contains one or more substances that cause signal transduction of Flt3 ligand signaling pathway. Such substances include, but not limited to, Flt3 ligand (Flt3L).

In some embodiments, the HPC induction media contains one or more substances that cause signal transduction of thrombopoietin signaling pathway. Such substances include, but not limited to, TPO.

The TGFβ inhibitor is a small molecule inhibitor that interferes with the signal transduction of TGFβ family and includes, for example, SB431542, SB202190 (both R. K. Lindemann et al., Mol. Cancer 2:20 (2003)), SB505124 (GlaxoSmithKline), NPC30345, SD093, SD908, SD208 (Scios), LY2109761, LY364947, LY580276 (Lilly Research Laboratories) and the like.

SB431542 is a potent and specific inhibitor of transforming growth factor-beta (TGFβ) superfamily type I activin receptor-like kinase (ALK) receptors ALK4, ALK5, and ALK7.

For example, when the TGFβ inhibitor is SB431542, its concentration in the medium is preferably 0.5 μM-100 μM The HPC induction media for the production of the HP cell bulk population may be further supplemented with a cytokine(s) selected from the group consisting of BMP4 (Bone morphogenetic protein 4), VEGF (vascular endothelial growth factor), bFGF (basic fibroblast growth factor), SCF (stem cell factor), TPO (thrombopoietin), and Flt3L (Flt3 ligand).

In one embodiment, the HPC induction media may include StemPro34 supplemented with human insulin (about 10 μg/ml), human transferrin (about 5.5 μg/ml), sodium selenite (about 6.7 ng/ml), L-glutamine (about 2 mM), «-monothioglycerol (about 0.4 mM), and SB431542 (about 6 μM).

In some embodiments, the vitamin C can be added every four days, every three days, every two days, or every day during the culture period. The addition of the vitamin C to the medium can be carried out at an amount corresponding to about 5 μg/ml to about 500 μg/ml. In some embodiments, vitamin C is present in the medium at about 5 μg/ml, 10 μg/ml, 25 μg/ml, 50 μg/ml, 100 μg/ml, 200 μg/ml, 300 μg/ml, 400 μg/ml, or 500 μg/ml.

In the specification, "vitamin C" means L-ascorbic acid and derivatives thereof, and "L-ascorbic acid derivative" means derivatives that become vitamin C by enzymatic reaction in the living body. Examples of the derivatives of L-ascorbic acid include vitamin C phosphate (e.g., ascorbic acid 2-phosphate), ascorbic acid glucoside, ascorbyl ethyl, vitamin C ester, ascorbyl tetrahexyldecanoate, ascorbyl stearate, and ascorbyl 2-phosphate 6-palmitate. Preferred is vitamin C phosphate. Examples of the vitamin C phosphate (e.g., ascorbic acid 2-phosphate) include salts of L-ascorbic acid phosphate such as L-ascorbic acid phosphate Na and L-ascorbic acid phosphate Mg.

In some embodiments, when the substances that cause signal transduction of bone morphogenetic protein 4 (BMP4) signaling pathway is BMP4, the concentration of the BMP4 in the HPC induction media for the production of the hematopoietic progenitor cells is about 5 ng/ml to 500 ng/ml, for example, 5 ng/ml, 10 ng/ml. 20 ng/ml, 30 ng/ml, 40 ng/ml, 50 ng/ml, 60 ng/ml, 70 ng/ml, 80 ng/ml, 90 ng/ml, 100 ng/ml, 150 ng/ml, 200 ng/ml, 250 ng/ml, 300 ng/ml, 350 ng/ml, 400 ng/ml, 450 ng/ml or 500 ng/ml.

In some embodiments, when the substances that cause signal transduction of vascular epithelial growth factor (VEGF) signaling pathway is VEGF, the concentration of the VEGF in the HPC induction media for the production of the hematopoietic progenitor cells is about 5 ng/ml to 500 ng/ml, for example, about 5 ng/ml 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 150 ng/ml, 200 ng/ml, 250 ng/ml, 300 ng/ml, 350 ng/ml, 400 ng/ml, 450 ng/ml or 500 ng/ml.

In some embodiments, when substances that cause signal transduction of fibroblast growth factor (FGF) pathway is bFGF, the concentration of the bFGF in the HPC induction media for the production of the hematopoietic progenitor cells is about 5 ng/ml to 500 ng/ml, for example, 5 ng/ml, 10 ng/ml, 20 ng/ml, 30 ng/ml, 40 ng/ml, 50 ng/ml, 60 ng/ml. 70 ng/ml, 80 ng/ml, 90 ng/ml. 100 ng/ml, 150 ng/ml. 200 ng/ml, 250 ng/ml, 300 ng/ml, 350 ng/ml, 400 ng/ml, 450 ng/ml or 500 ng/ml.

In some embodiments, when the substances that cause signal transduction of stem cell factor/kit signaling pathway is SCR, the concentration of the SCF in the HPC induction media for the production of the hematopoietic progenitor cells is about 5 ng/ml to 100 ng/ml, for example, 5 ng/ml, 10 ng/ml, 20 ng/ml, 30 ng/ml, 40 ng/ml, 50 ng/ml, 60 ng/ml, 70 ng/ml, 80 ng/ml, 90 ng/ml, or 100 ng/ml.

In some embodiments, when the substances that cause signal transduction of Flt3 ligand signaling pathway is Flt3L, the concentration of the Flt3L in the HPC induction media for the production of the hematopoietic progenitor cells is about 1 ng/ml to 100 ng/ml, for example, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 20 ng/ml, 50 ng/ml, or 100 ng/ml.

In some embodiments, when the substances that cause signal transduction of thrombopoietin signaling pathway is TPO, the concentration of the TPO in the HPC induction media for the production of the hematopoietic progenitor cells is about 1 ng/ml to 200 ng/ml, for example, 1 ng/ml, 2 ng/ml, 3 ng/ml, 4 ng/ml. 5 ng/ml, 6 ng/ml, 7 ng/ml, 8 ng/ml, 9 ng/ml, 10 ng/ml, 20 ng/ml, 30 ng/ml, 40 ng/ml, 50 ng/ml, 60 ng/ml. 70 ng/ml, 80 ng/ml, 90 ng/ml, 100, 125 ng/ml, 150 ng/ml, 175 ng/ml, or 200 ng/ml.

In some embodiments, the pluripotent stem cells may be cultured by adherent culture or suspension culture. In cases of adherent culture, the culture may be carried out in a culture vessel coated with a coating agent, and/or may be co-cultured with other cells. Examples of other cells for the co-culture include C3H10T1/2 (Takayama N., et al. J Exp Med. 2817-2830, 2010) and stromal cells derived from a different species (Niwa A et al. J Cell Physiol. 2009 November; 221 (2): 367-77). Examples of the coating agent include Matrigel (*Nivea* A, et al. PLOS One. 6 (7): e22261, 2011), iMatrix 511 (Miyazaki T, et al. Nature Communication 2012; 3:1236), gelatin, collagen, elastin and the like, glucosaminoglycan and proteoglycan such as hyaluronic acid, chondroitin sulfate and the like, cell adhesion proteins such as fibronectin or a variant thereof, vitronectin, laminin and the like, and the like. Examples of the method of the suspension culture include the methods described in Chadwick et al. Blood 2003, 102:906-15, Vijayaragavan et al. Cell Stem Cell 2009, 4:248-62, and Sacki et al. Stem Cells 2009, 27:59-67.

In some embodiments, the HP cell bulk can also be prepared from a net-like structure (which is also referred to as ES-sac or iPS-sac) obtained by culture of pluripotent stem cells. The "net-like structure" herein is a three-dimensional sac-shaped structure (having a space in the inside) derived from pluripotent stem cells. The structure is formed with an endothelial cell population or the like, and contains hematopoietic progenitor cells in the inside.

In some embodiments, the temperature conditions for the culture for production of the HP cell bulk is from about 37° C. to about 42° C. In some embodiments, the temperature is, for example, about 37° C. to about 42° C., preferably about 37 to about 39° C. The culture period may be appropriately determined by those skilled in the art by monitoring of the number of hematopoietic progenitor cells and/or the like by obtaining a sample from the cell culture for phenotypic analysis. Various kinds of methods are known in the art related to phenotypic analysis of cell samples and include, for example, flow cytometry and immunofluorescence methods.

The culture period to obtain HP cell bulk may vary and include, for example, between 6 and 14 days. Examples of the culture period include at least 6 days, not less than 7 days, not less than 8 days, not less than 9 days, not less than 10 days, not less than 11 days, not less than 12 days, not less than 13 days, and not less than 14 days. In some embodiments, the culture period is for six days. In some embodiments, the culture period is 7 days. In some embodiments, the culture period is 8 days. In some embodiments, the culture period is 9 days. In some embodiments, the culture period is 10 days. In some embodiments, the culture period is 10 days. In some embodiments, the culture period is 11 days. In some embodiments, the culture period is 12 days. In some embodiments, the culture period is 13 days. In some embodiments, the culture period is 14 days. In some embodiments, the culture period is for greater than 14 days. The culture may be carried out under low-oxygen conditions. Examples of the low-oxygen conditions include 15%, 10%, 9%, 8%, 7%, 6%, 5%, 4%, 3% or lower. Frequency of medium change can be decided by a person skilled in the art. In some embodiments, medium can be changed after every 2 days. In some other embodiments, medium can be changed after every 3 days. In some embodiments, the medium is changed every day.

In some embodiments, the culture for the production of the HP cell bulk is carried out by combining one or more of the above conditions. For example, in some embodiments, the method to obtain HP cell bulk from iPSC comprises: (i) culturing pluripotent stem cells on C3H10T1/2 in a basal medium supplemented with vitamin C under low-oxygen conditions; and (ii) further adding VEGF, SCF, and Flt3L to the culture liquid of (1), and culturing the cells under normal oxygen conditions. The period during which the step (i) is carried out is at least not less than six days, preferably not less than seven days, more preferably seven days. The period during which the step (ii) is carried out is at least not less than six days, not less than seven days, and for seven days.

In some embodiments, the hematopoietic progenitor cells obtained in the HP cell bulk may be isolated before further use. In some other embodiments, the hematopoietic progenitor cells obtained may be used as a cell population that also contains other cell species (HP cell bulk). The HP cell bulk population is an unseparated cell preparation. In some embodiments, the method does not comprise an isolation step.

Culture Conditions—HP Cell Bulk to CD4/CD8 Cells

In some embodiments, the CD4/CD8 induction medium results in a cell population comprising CD4+/CD8+, CD4−/CD8− cells, CD4−/CD8+ cells, and CD4+/CD8− cells. "CD4/CD8 double-positive cells" (DP cells) means cells that express both CD4 and CD8. CD4/CD8 double-positive cells can be identified as cells which are CD4, CD8, CD3, and CD45 positive. "CD4/CD8 double-negative cells" (DN cells) means cells that do not express both CD4− and CD8−. "CD4−/CD8+ cells" means cells that do not express CD4− but express CD8+. "CD4+/CD8− cells" means cells that express CD4 but do not express CD8.

In some embodiments, the cell population comprising CD4+/CD8+, CD4−/CD8− cells, CD4−/CD8+ cells, and CD4+/CD8− cells can be induced to differentiate into CD56+/CD3− cells.

In some embodiments, a cell population comprising CD4/CD8 double-positive cells, among other cells, can be produced by a method that includes a step of culturing hematopoietic progenitor cells or HP cell bulk in a medium supplemented with vitamin C. The vitamin C to be added to the basal medium is the same as that in the above-described induction of HP cell bulk.

In some embodiments, medium used to produce a cell population comprising CD4+/CD8+, CD4−/CD8− cells, CD4−/CD8+ cells, and CD4+/CD8− cells from the HP cell bulk is the CD4/CD8 induction medium. In some embodiments, the CD4/CD8 induction medium may be prepared by adding vitamin C to a basal medium which is used for culture of animal cells. Examples of the basal medium include Iscove's Modified Dulbecco's Medium (IMDM), Medium 199, Eagle's Minimum Essential Medium (EMEM), αMEM medium (Thermo Fisher Scientific (Gibco)), Dulbecco's modified Eagle's Medium (DMEM), Ham's F12 medium, RPMI 1640 medium, Fischer's medium, and Neurobasal Medium (Life Technologies), and mixtures of two or more of these media. The medium may contain serum, or may be serum-free.

If necessary, the basal medium may also contain one or more of substances such as albumin, human insulin, human transferrin, selenium, sodium selenite, fatty acid, trace elements, 2-mercaptoethanol, thiol glycerol, lipids, amino acids, L-glutamine, non-essential amino acids, vitamins, growth factors, low molecular-weight compounds, antibiotics, antioxidants, pyruvic acrid, buffers, inorganic salts, and cytokines.

The CD4/CD8 induction medium for the production of a cell population comprising CD4/CD8 double-positive cells, among other cells, may be further supplemented with a cytokine(s) selected from the group consisting of ascorbic acid, SCF, IL-7, Flt3L, TPO, fibronectin or a variant thereof, Notch ligand, p38 inhibitor and SDF-1.

In some embodiments, the vitamin C can be added every four days, every three days, every two days, or every day during the culture period. The addition of the vitamin C to the medium can be carried out at an amount corresponding to about 5 µg/ml to about 500 µg/ml. In some embodiments, vitamin C is present in the medium at about 5 µg/ml, 10 µg/ml, 25 µg/ml, 50 µg/ml, 100 µg/ml, 200 µg/ml, 300 µg/ml, 400 µg/ml, or 500 µg/ml.

In some embodiments, the basal medium contains one or more substances that cause signal transduction of stem cell factor/kit signaling pathway. Such substances include, but not limited to, SCF.

In some embodiments, the basal medium contains one or more substances that cause signal transduction of Flt3 ligand signaling pathway. Such substances include, but not limited to, Flt3 ligand (Flt3L).

In some embodiments, the basal medium contains one or more substances that cause signal transduction of thrombopoietin signaling pathway. Such substances include, but not limited to, TPO.

In some embodiments, the basal medium contains one or more p38 inhibitor which is an inhibitor of p38a and p38B which in turn suppresses downstream activation of MAPKAP kinase-2 and heat shock protein 27. Examples of the chemical inhibitor of p38 to be used in the present invention include, but are not limited to, SB203580 (4-(4-fluorophenyl)-2-(4-methylsulfonylphenyl)-5-(4-pyridyl)-1H-imidazole), and a derivative thereof, SB202190 (4-(4-fluorophenyl)-2-(4-hydroxyphenyl)-5-(4-pyridyl)-1H-imidazole) and a derivative thereof, SB239063 (trans-4-[4-(4-fluorophenyl)-5-(2-methoxy-4-pyrimidinyl)-1H-imidazol-1-yl]cyclohexanol) and a derivative thereof, SB220025 and a derivative thereof, PD169316, RPR200765A, AMG-548, BIRB-796, SCIO-469, SCIO-323, VX-702 and FR167653. These compounds are commercially available and, for example, SB203580, SB202190, SC239063, SB220025 and PD169316 are available from Calbiochem, and SCIO-469 and SCIO-323 are available from Scios and the like. Other examples of p38 inhibitors comprise the dominant-negative mutant of p38 which includes p38T180A obtained by point mutation of the 180-position threonine located in the DNA binding region of p38 to alanine, p38Y182F obtained by point mutation of the 182-position tyrosine of p38 in human and mouse to phenylalanine and the like. The p38 inhibitor is contained in a medium at, for example, about 0.5 µM-about 50 µM.

In some embodiments, the basal medium contains SDF-1.

In some embodiments, SDF-1 may be not only SDF-1α or a mature form thereof, but also an isoform such as SDF-1β, SDF-1γ, SDF-1δ, SDF-1ε, SDF-1φ and the like or a mature form thereof, or a mixture of these at any ratio or the like. Preferably, SDF-1α is used. SDF-1 is sometimes referred to as CXCL-12 or PBSF.

In some embodiments, one or several amino acids in the amino acid sequence of SDF-1 may be substituted, deleted and/or added as long as it has the activity as the chemokine, and similarly, the sugar chain may be substituted, deleted and/or added. An amino acid mutation is acceptable as long as at least 4 cysteine residues (Cys30, Cys32, Cys55 and Cys71 in human SDF-1α) are maintained and not less than 90% identity with amino acid sequence of a natural substance is exhibited. SDF-1 may be obtained from a mammal, for example, human or non-human mammal such as monkey, sheep, bovine, horse, swine, dog, cat, rabbit, rat, mouse and the like. For example, the protein registered as GenBank accession number: NP_954637 can be used as human SDF-1a, and the protein registered as GenBank accession number: NP_000600 can be used as SDF-1B. In some embodiments, when the substances that cause signal transduction of Flt3 ligand signaling pathway is Flt3L, the concentration of the Flt3L in the medium for the production of a cell population comprising CD4/CD8 double-positive cells is about 1 ng/ml to 100 ng/ml, for example, 1 ng/ml, 2 ng/ml, 3 ng/ml, 4 ng/ml, 5 ng/ml, 6 ng/ml, 7 ng/ml, 8 ng/ml, 9 ng/ml. 10 ng/ml, 20 ng/ml, 30 ng/ml, 40 ng/ml, 50 ng/ml, 60 ng/ml, 70 ng/ml, 80 ng/ml, 90 ng/ml, or 100 ng/ml.

In some embodiments, when the substances that cause signal transduction of stem cell factor/kit signaling pathway is SCF, the SCF is used for the production of cell population comprising CD4/CD8 double-positive cells under the same conditions as described above.

In some embodiments, when the substances that cause signal transduction of thrombopoietin signaling pathway is TPO, the TPO is used for the production cell population comprising CD4/CD8 double-positive cells under the same conditions as described above.

Fibronectin or a variant thereof to be used in the invention is not particularly limited as long as it is a molecule capable of binding to CD3 positive cells. The variant of fibronectin is not particularly limited as long as it is a molecule capable of binding to VLA-5 and VLA-4 on the surface of CD3 positive cells, and examples thereof include RetroNectin. Fibronectin and a variant thereof may be present in any form in the medium. For example, they may be contained in the medium during culture, or may be immobilized on a culture container, and are preferably immobilized on a culture container.

When fibronectin or a variant thereof is contained in a medium, the lower limit of the concentration of fibronectin or a variant thereof may be not less than 10 ng/ml, preferably not less than 100 ng/ml, and the upper limit may be not more than 10000 μg/ml, preferably not more than 1000 μg/ml.

In some embodiments, the concentration of the IL-7 in the medium to be used for the production of cell population comprising CD4/CD8 double-positive cells is about 1 ng/ml to 100 ng/ml, for example, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 20 ng/ml, 30 ng/ml, 40 ng/ml, 50 ng/ml, 60 ng/ml, 70 ng/ml, 80 ng/ml, 90 ng/ml, or 100 ng/ml.

SDF-1 may be commercially available, purified from nature, or produced by peptide synthesis or genetic engineering techniques. SDF-1 is contained in a medium within the range of, for example, about 10 ng/ml to about 100 ng/ml. In addition, SDF-1 alternative having an SDF-1-like activity can also be used instead of SDF-1. Examples of such SDF-1 alternative include CXCR4 agonist, and a low-molecular-weight compound having a CXCR4 agonist activity and the like may be added to the medium instead of SDF-1.

In some embodiments, when the SDF-1 is SDF1a, the concentration of the SDF-1α in the medium for the production of cell population comprising CD4/CD8 double-positive cells is about 1 nM to 100 nM, for example, 1 nM, 2 nM, 3 nM, 4 nM, 5 nM, 6 nM, 7 nM, 8 nM, 9 nM, 10 nM, 20 nM, 30 nM, 40 nM, 50 nM, 60 nM, 70 nM, 80 nM, 90 nM, or 100 nM.

In some embodiments, when the p38 inhibitor is SB203580, the concentration of the SB203580 in the medium for the production of cell population comprising CD4/CD8 double-positive cells is about 0.5 μM to 100 μM, for example, 0.5 μM, 1 μM, 2 μM, 3 μM, 4 μM, 5 μM, 6 μM, 7 μM, 8 μM, 9 μM, 10 μM, 15 μM, 20 μM, 30 μM, 40 μM, or 50 μM, 60 μM, 70 μM, 80 μM, 90 μM, or 100 μM.

In some embodiments, the basal medium for production of cell population comprising CD4/CD8 double-positive cells includes αMEM medium supplemented with about 15% FBS, about 4 mM L-glutamine, about 100 U/ml penicillin, about 100 μg/ml streptomycin, about 55 μM 2-mercaptoethanol, about 50 μg/ml ascorbic acid 2-phosphate, about 10 μg/ml human insulin, about 5.5 μg/ml human transferrin, about 6.7 ng/ml sodium selenite, about 50 ng/ml SCF, about 50 ng/ml IL-7, about 50 ng/ml Flt3L, about 100 ng/ml TPO, about 15 μM SB203580, about 30 nM SDF-1a.

In the production of a cell population comprising CD4/CD8 double-positive cells, the hematopoietic progenitor cells may be cultured by adherent culture or suspension culture. In some embodiments, the culture vessel/dish is coated with DLL1 or DLL4, or a fusion protein of DLL4 or DLL1, and Fc or the like. DLL1 or DLL4 may be recombinant human (rh)-DLL1 or rh-DLL4. In some embodiments, the culture vessel/dish is coated with rh-DLL4/Fc chimera (Sino Biological) and RetroNectin (Takara Bio Inc). In cases of adherent culture, a coated culture vessel may be used, and/or the hematopoietic progenitor cells may be co-cultured with feeder cells and/or the like. Examples of the feeder cells for the co-culture include a bone-marrow stromal cell line, OP9 cells (available from Riken BioResource Center). The OP9 cells may be preferably OP-DLI cells, which constantly express Dlll (Holmes R I and Zuniga-Pflucker J C. Cold Spring Harb Protoc. 2009 (2)). In some embodiments, where OP9 cells are used as the feeder cells, Dill, or a fusion protein of Dlll and Fc or the like, separately prepared may be added to the medium to perform the co-culture. In some embodiments. Dlll can include proteins encoded by a gene having the nucleotide sequence of the NCBI accession number NM #005618 in the case of human, or NCBI accession number NM #007865 in the case of mouse; and naturally occurring mutants having a high sequence identity (for example, having a sequence identity of not less than 90%) to these proteins and having an equivalent function. In cases where feeder cells are used for production a cell population comprising CD4/CD8 double-positive cells, the feeder cells can be appropriately replaced during the culture. The replacement of the feeder cells may be carried out by transferring the subject cells that are being cultured onto feeder cells that are preliminarily plated. The replacement may be carried out every five days, every four days, every three days, or every two days.

In some embodiments, the culture temperature conditions for the culture of the HP cell bulk for production of a cell population comprising CD4/CD8 double-positive cells is about 37° C. to about 42° C., and about 37 to about 39° C. In some embodiments, the culture may be carried out under low-oxygen conditions. Examples of the low-oxygen conditions include 15%, 10%, 9%, 8%, 7%, 6%, 5%, and oxygen concentrations lower than these. The culture period may be appropriately determined by those skilled in the art by monitoring of the number of different types of cells including CD4/CD8 double-positive cells and/or the like. Examples of the culture period include not less than 10 days, not less than 12 days, not less than 14 days, not less than 16 days, not less than 18 days, not less than 20 days, not less than 21 days, not less than 23 days, not less than 25 days, not less than 28 days, not less than 30 days, not less than 35 days, or not less than 42 days. In some other embodiments, the CD4/CD8 double-positive cells obtained from the culturing is a cell population that also contains other cell species (DP cell bulk).

In cases where a population of a particular cell type (e.g., CD4−/CD8+ cells) from a cell population comprising the CD4/CD8 double-positive cells are isolated, the isolation may be carried out using any one index including but not limited to, CD4, CD8, CD3, and CD45, depending on the cell type being isolated. The isolation method may be a method well known to those skilled in the art, for example, a method in which the cells are labeled with a particular antibody (e.g., CD4, CD8, CD3, or CD45 antibody), and then isolated using a flow cytometer, or a method in which the cells are purified using an affinity column or the like to which a desired antigen is immobilized.

Step of Inducing CD56+/CD3-Cells from a Cell Population Comprising CD4/CD8 Double-Positive Cells In some embodiments, NK cells are CD56+/CD3− immune cells.

In some embodiments, the NK cells are produced by a method comprising the step of culturing a cell population comprising CD4/CD8 double-positive cells or DP cell bulk in a medium supplemented with vitamin C. In some embodiments, the NK induction media is used to produce the CD56+/CD3− cells.

In some embodiments, the medium is prepared by adding vitamin C to a basal medium which is used for culture of animal cells. Examples of the basal medium include Iscove's Modified Dulbecco's Medium (IMDM), Medium 199, Eagle's Minimum Essential Medium (EMEM), αMEM medium, Dulbecco's modified Eagle's Medium (DMEM), Ham's F12 medium, RPMI 1640 medium, Fischer's medium, and Neurobasal Medium (Life Technologies), and mixtures of two or more of these media. In some embodiments, the medium contains serum. In some embodiments, the medium is serum-free. If necessary, the basal medium may also contain one or more of substances such as albumin, human insulin, human transferrin, selenium or sodium selenite, fatty acid, trace elements, 2-mercaptoethanol, thiol glycerol, lipids, amino acids, glutamine, non-essential amino acids, vitamins, growth factors, low-molecular-weight compounds, antibiotics, antioxidants, pyruvic acid, buffers, inorganic salts, and cytokines.

In some embodiments, the medium used for the production of the CD56 positive NK cells further contains an anti-CD3 antibody (UCHT1) and cytokines. Examples of the suitable cytokines include IL-2 and IL-7.

The CD3 antibody is not limited as long as it specifically recognizes CD3. In some embodiments, the concentration of the CD3 antibody in the NK induction media is about 10 ng/ml to 1000 ng/ml, for example, 10 ng/ml, 50 ng/ml, 100 ng/ml, 200 ng/ml, 300 ng/ml, 400 ng/ml. 500 ng/ml, 600 ng/ml, 700 ng/ml, 800 rig/ml, 900 ng/ml, or 1000 ng/ml.

In some embodiments, vitamin C is used for the production of the CD56 positive K cells under the same conditions as described above.

In some embodiments, the concentration of the IL-2 in the NK induction media for the production of the CD56 positive NK cells is about 1 U/ml to 1000 U/ml, for example, about 1 U/ml, 5 U/ml, 10 U/ml. 20 U/ml, 30 U/ml, 40 U/ml, 50 U/ml, 60 U/ml, 70 U/ml, 80 U/ml, 90 U/ml, 100 U/ml, 500 U/ml, or 1000 U/ml. In some embodiments, the concentration of the IL-2 in the NK induction media for the production of the CD56 positive NK cells is about 1 ng/ml to 100 ng/ml, for example, 1 ng/ml, 5 ng/ml, 10 ng/ml, 20 ng/ml, 30 ng/ml, 40 ng/ml, 50 ng/ml, 60 ng/ml, 70 ng/ml, 80 ng/ml, 90 ng/ml, or 100 ng/ml.

In some embodiments, the concentration of the IL-7 in the NK induction media for the production of the CD56 positive NK cells is about 1 ng/ml to 100 ng/ml, for example, 1 ng/ml, 5 ng/ml, 10 ng/ml, 20 ng/ml, 30 ng/ml, 40 ng/ml. 50 ng/ml, 60 ng/ml, 70 ng/ml, 80 ng/ml, 90 ng/ml, or 100 ng/ml.

In some embodiments, the culture temperature conditions for the culture of the a population comprising CD4/CD8 double-positive cells for production of the CD56 positive NK cells is about 37° C. to about 42° C., or about 37 to about 39° C. The culture period may be appropriately determined by those skilled in the art by monitoring of the number of CD56 positive NK cells and/or the like. The number of days of the culture is not limited as long as CD56 positive NK cells can be obtained. Examples of the culture period include at least not less than 1 day, not less than 2 days, not less than 3 days, not less than 4 days, not less than 5 days, not less than 6 days, or not less than 7 days.

In some embodiments, the CD56+NK cells obtained may be isolated before further use. In some other embodiments, the CD56 positive NK cells obtained may be used as a cell population that also contains other cell species, including T cells (NK cell bulk).

In some embodiments, NK cell bulk may include 50%, 55%, 60%, 75%, 80%, 85%, 90%, or more than 90% NK cells. In some embodiments, NK cell bulk includes about 10%, 15%, 20%, 25%, 30%, 35%, 40%, 45%, or, 50% T cells. In some embodiments, NK cell bulk includes about 75% CD56+/CD3− NK cells and about 25% CD56+/CD3+ T cells. In some embodiments, NK cell bulk may also include B cells and monocytes.

In cases where the CD56+NK cells are isolated, the isolation method may be a method well known to those skilled in the art, for example, a method in which the cells are labeled with an anti-CD56 antibody and anti-CD3 antibody, and then isolated using a flow cytometer (fluorescence-activated cell sorting), or a method in which the cells are purified using an affinity column or the like to which a desired antigen is immobilized.

In some embodiments, the CD56 positive NK cells are CD56+/CD3+. In some embodiments, the CD56 positive NK cells are CD56+/CD3−.

CAR-NK Cell Preparation

In some embodiments, the NK cell are engineered to comprise one or more transgenes. For example, the NK cells can be genetically engineered to express tumor-directed chimeric antigen receptors (CAR), thereby producing anti-tumor effector cells. In one example, the NK cell or iPS NK cell can be engineered to express CAR. In some embodiments, a cell precursor to the NK cell is engineered to express a CAR. For example, in some embodiments, the iPS cell is engineered to express a CAR. In some embodiments, cells in the HP cell bulk are engineered to express a CAR. In some embodiments, the NK cell is engineered to express a CAR. Moreover, in some embodiments, these transgenic receptors can be directed to tumor-associated antigens that are not protein-derived. In certain embodiments, NK cells or iPS NK cells are modified to comprise at least one CAR. In some embodiments, a single CAR targets two or more antigens.

In some embodiments, the iNK cells include a receptor that is chimeric, non-natural and engineered. In some embodiments, the engineered chimeric antigen receptor (CAR) has one, two, three, four, or more components, and in some embodiments the one or more components facilitate targeting or binding of the lymphocyte to one or more tumor antigen-comprising cancer cells.

In some embodiments, the CAR generally comprises at least one transmembrane polypeptide comprising at least one extracellular ligand-biding domain and; one transmembrane polypeptide comprising at least one intracellular signaling domain; such that the polypeptides assemble together to form a Chimeric Antigen Receptor.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state.

In particular, the extracellular ligand-binding domain can comprise an antigen binding domain derived from an antibody against an antigen of the target.

In some embodiments, NK cells or iPS NK cells can be genetically modified to express one or more chimeric antigen receptors (CAR). In some embodiments, the CAR includes an extracellular ligand-binding domain that targets a tumor antigen selected from one or more of the following: CD44, CD19, CD20, CD22, CD23, CD30, CD89, CD123, CS-1, ROR1, mesothelin, c-Met, PSMA, Her2, GD-2, CEA, MAGE A3 TCR, EGFR, HER2/ERBB2/neu, EPCAM, EphA2, CEA, BCMA. In some embodiments, the tumor antigen is CD19.

In some embodiments, the extracellular ligand-binding domain is a single chain antibody fragment (scFv) comprising the light (VL) and the heavy (VH) variable fragment of a target antigen specific monoclonal antibody joined by a flexible linker.

In some embodiments, the CAR includes a transmembrane domain. In some embodiments, transmembrane domain further comprises a stalk region between the extracellular ligand-binding domain and the transmembrane domain. The term "stalk region" used herein generally means any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, 10 to 100 amino acids, and/or 25 to 50 amino acids. A stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence. In a preferred embodiment said stalk region is a part of human CD8 alpha chain In some embodiments, the CAR contains a signal transducing domain or intracellular signaling domain which contributes to intracellular signaling following the binding of extracellular ligand binding domain to the target resulting in the activation of the iPS NK cell and immune response. The term "signal transducing domain" refers to the portion of a protein which transduces the effector signal function signal and directs the cell to perform a specialized function. In some embodiments, iPS NK cells have a CAR that includes a signal transducing domain.

In some embodiments, the iPS NK cell are genetically modified to express IL-15Rα/IL-15 complex.

In some embodiments, transmembrane polypeptides comprise the ability to be expressed at the surface of an immune cell, for example on iPS NK cells, and to interact together for directing cellular response of immune cell against a predefined target cell. The different transmembrane polypeptides of the CAR comprising an extracellular ligand-biding domain and/or a signal transducing domain interact together to take part in signal transduction following the binding with a target ligand and induce an immune response. The transmembrane domain can be derived either from a natural or from a synthetic source. The transmembrane domain can be derived from any membrane-bound or transmembrane protein.

In some embodiments, genetic modification of NK cells to express CAR can include steps of: (1) synthesizing a gene corresponding to a specific CAR; (2) preparing a vector containing the gene corresponding to the CAR; and (3) transducing the CD56+NK cells with the vector containing the CAR gene.

Expression vectors that encode the CARs can be introduced as one or more DNA molecules or constructs, where there may be at least one marker that will allow for selection of host cells that contain the construct(s).

The constructs can be prepared in conventional ways, where the genes and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc., as appropriate. The construct(s) once completed and demonstrated to have the appropriate sequences may then be introduced into the CTL by any convenient means. The constructs may be integrated and packaged into non-replicating, defective viral genomes like Adenovirus, Adeno-associated virus (AAV), or Herpes simplex virus (HSV) or others, including retroviral vectors or lentiviral vectors, for infection or transduction into cells. The constructs may include viral sequences for transfection, if desired. Alternatively, the construct may be introduced by fusion, electroporation, biolistics, transfection, lipofection, or the like. The host cells may be grown and expanded in culture before introduction of the construct(s), followed by the appropriate treatment for introduction of the construct(s) and integration of the construct(s). The cells are then expanded and screened by virtue of a marker present in the construct. Various markers that may be used successfully include hprt, neomycin resistance, thymidine kinase, hygromycin resistance, etc.

In some instances, one may have a target site for homologous recombination, where it is desired that a construct be integrated at a particular locus. For example, can knock-out an endogenous gene and replace it (at the same locus or elsewhere) with the gene encoded for by the construct using materials and methods as are known in the art for homologous recombination. For homologous recombination, one may use either .OMEGA. or O-vectors.

The constructs may be introduced as a single DNA molecule encoding at least the CAR and optionally another gene, or different DNA molecules having one or more genes. Other genes include genes that encode therapeutic molecules or suicide genes, for example. The constructs may be introduced simultaneously or consecutively, each with the same or different markers.

Vectors containing useful elements such as bacterial or yeast origins of replication, selectable and/or amplifiable markers, promoter/enhancer elements for expression in prokaryotes or eukaryotes, etc. that may be used to prepare stocks of construct DNAs and for carrying out transfections are well known in the art, and many are commercially available.

Methods of Use

The cells according to the invention can be used for treating cancer, viral infections or autoimmune disorders in a patient in need thereof. In another embodiment, said isolated cell according to the invention can be used in the manufacture of a medicament for treatment of a cancer, viral infections of autoimmune disorders, in a patient in need thereof.

The present invention relies on methods for treating patients in need thereof, said method comprising at least one of the following steps: (a) providing a chimeric antigen receptor cells according to the invention and (b) administrating the cells to said patient.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

In some embodiments, the described cells are allogeneic. In some embodiments, the described cells are autologous.

Treatment can be used to treat patients diagnosed with cancer, viral infection, autoimmune disorders or Graft versus Host Disease (GvHD). Cancers that may be treated include tumors that are not vascularized, or not yet substantially vascularized, as well as vascularized tumors. The cancers may comprise nonsolid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

In some embodiments, treatment is in combination with one or more therapies against cancer selected from the group of antibodies therapy, chemotherapy, cytokines therapy, dendritic cell therapy, gene therapy, hormone therapy, laser light therapy and radiation therapy.

In some embodiments, said treatment can be administered into patients undergoing an immunosuppressive treatment.

In a further embodiment, the cell compositions are administered to a patient in combination with one or more additional therapies. For example, in some embodiments, the cell compositions are administered to a patient in conjunction with (e.g., before, simultaneously or following) bone marrow transplantation. T cell ablative therapy using either chemotherapy agents such as, fludarabine, external-beam radiation therapy (XRT), cyclophosphamide, or antibodies such as OKT3 or CAM PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery. Said modified cells obtained by any one of the methods described here can be used in a particular aspect of the invention for treating patients in need thereof against Host versus Graft (HvG) rejection and Graft versus Host Disease (GvHD); therefore in the scope of the present invention is a method of treating patients in need thereof against Host versus Graft (HvG) rejection and Graft versus Host Disease (GvHD) comprising treating said patient by administering to said patient an effective amount of modified cells comprising inactivated TCR alpha and/or TCR beta genes.

Administration of Cells

In some embodiments, the cells can be introduced into a host organism, e.g. a mammal, in a wide variety of ways. The cells may be introduced at the site of the tumor, in specific embodiments, although in alternative embodiments the cells hone to the cancer or are modified to hone to the cancer. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest. The cells may be in a physiologically-acceptable medium. In one example, the NK cells or iPS NK cells of the present invention may express one or more CARs. TCRs, or any other engineered protein or polypeptide domain such as high affinity CD16. In some embodiments, the cells are encapsulated to inhibit immune recognition and placed at the site of the tumor.

The cells may be administered as desired. Depending upon the response desired, the manner of administration, the life of the cells, the number of cells present, various protocols may be employed. The number of administrations will depend upon the factors described above at least in part.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

Nucleic Acid-Based Expression Systems

In some embodiments, the NK cells or iPS NK cells of the invention are engineered to express one or more CARs, TCRs, or any other engineered protein or polypeptide domain such as high affinity CD16 or CD19. Recombinant techniques to generate expression vectors comprising these polypeptides are well known in the art and are described generally below.

Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned." "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5 prime' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring." i.e., containing different elements of different transcriptional regulatory regions, and/or mutations that alter expression. For example, promoters that are most commonly used in recombinant DNA construction include the lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals In certain embodiments of the invention, the use of internal ribosome entry sites (IRES) elements are used to create multigene, or polycistronic, messages, and these may be used in the invention.

Vectors can include a multiple cloning site (MCS), which is a nucleic acid region that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing sites, termination signals, origins of replication, and selectable markers may also be employed.

Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™ 11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Components of the present invention may be a viral vector that encodes one or more CARs, TCR, or any other engineered protein or polypeptide domain such as high affinity CD16 of the invention. Non-limiting examples of virus vectors that may be used to deliver a nucleic acid of the present invention are described below.

Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the cells of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; Mclaughlin et al., 1988). Details concerning the generation and use of rAAV vectors are described in U.S. Pat. Nos. 5,139,941 and 4,797,368, each incorporated herein by reference.

Retroviral Vectors

Retroviruses are useful as delivery vectors because of their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid (e.g., one encoding the desired sequence) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

Combination Therapy

In certain embodiments of the invention, methods of the present invention for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with other therapies. In the context of the present invention, it is contemplated that cell therapy could be used similarly in conjunction with chemotherapeutic, radiotherapeutic, or immunotherapeutic intervention, as well as pro-apoptotic or cell cycle regulating agents.

Alternatively, the therapy may precede or follow the other agent treatment by intervals ranging from minutes to weeks. In embodiments where the other agent and present invention are applied separately to the individual, one would generally ensure that a significant period of time did not expire between the time of each delivery, such that the agent and inventive therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

In some embodiments, the treatment cycles are repeated as necessary. It also is contemplated that various standard therapies, as well as surgical intervention, may be applied in combination with the inventive cell therapy.

Chemotherapy

Cancer therapies also include a variety of combination therapies with both chemical and radiation based treatments. Combination chemotherapies include, for example, abraxane, altretamine, docetaxel, herceptin, methotrexate, novantrone, zoladex, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing and also combinations thereof.

In specific embodiments, chemotherapy for the individual is employed in conjunction with the invention, for example before, during and/or after administration of the invention Radiotherapy Other factors that cause DNA damage and have been used extensively include what are commonly known as .gamma.-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Immunotherapy

Immunotherapeutics generally rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy other than the inventive therapy described herein could thus be used as part of a combined therapy, in conjunction with the present cell therapy. The general approach for combined therapy is discussed below. Generally, the tumor cell must bear some marker that is amenable to targeting. i.e., is not present on the majority of other cells. Many tumor markers exist and any of these may be suitable for targeting in the context of the present invention. Common tumor markers include PD-1, PD-L1, CTLA4, carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Genes

In yet another embodiment, the secondary treatment is a gene therapy in which a therapeutic polynucleotide is administered before, after, or at the same time as the present invention clinical embodiments. A variety of expression products are encompassed within the invention, including inducers of cellular proliferation, inhibitors of cellular proliferation, or regulators of programmed cell death.

Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

EXAMPLES

Other features, objects, and advantages of the present invention are apparent in the examples that follow. It should be understood, however, that the examples, while indicating embodiments of the present invention, are given by way of illustration only, not limitation. Various changes and modifications within the scope of the invention will become apparent to those skilled in the art from the examples.

Example 1. Differentiation of iPS Cells into HP Cell Bulk

FfI-01s04 strain, an iPS cell strain, was derived from peripheral blood mononuclear cell of a healthy individual. FfI-01s04 cells dispersed in StemFit complete medium was seeded at $6 \times 10^5$ cells/well in an ultra-low adhesion-treated 6 well plate under a low-oxygen (5% $O_2$) condition ("Day 0"). The StemFit complete medium included 10 µM CHIR99021 and 50 µM Y-27632. Next day (i.e., Day 1), the FfI-01s04 cells were dispersed in a hematopoietic progenitor cells (HPC) differentiation medium containing BMP4 (50 ng/ml), VEGF (50 ng/ml), bFGF (50 ng/ml), and ascorbic acid 2-phosphate (50 µg/ml). The HPC induction medium medium included StemPro34 supplemented with human insulin (10 µg/ml), human transferrin (5.5 µg/ml), sodium selenite (6.7 ng/ml), L-glutamine (2 mM) and α-monothioglycerol (0.4 mM). On Day 2, SB431542 (at 6 µM in medium) was added to the culture medium (i.e., HPC differentiation medium containing cells), and the cells were cultured for 2 days. On Day 4, cells were redispersed in another medium containing VEGF (50 ng/ml), bFGF (50 ng/ml), SCF (50 ng/ml), and ascorbic acid 2-phosphate (50 µg/ml), and cultured for further 3 days. On Day 7, cells were exposed to another medium containing VEGF (50 ng/ml), bFGF (50 ng/ml), SCF (50 ng/ml), ascorbic acid 2-phosphate (50 µg/ml), TPO (30 ng/ml) and Flt3L (10 ng/ml), and cultured using this medium for additional 7 days. The medium was changed every 2-3 days during this 7 days-culture period.

Example 2. Differentiation of HP Cell Bulk into Population Comprising CD4/CD8 Cells At Day 14, the cell population obtained from Example 1 without undergoing any cell isolation ("HP cell bulk") was seeded in 15 cm dishes at $3.12 \times 10^6$ cells/dish, and cultured at 37° C. under 5% $O_2$. It is noted that various seeding densities may be used, and the aforementioned seeding density is one embodiment. Each 15 cm dish was coated with rh-DLL4/Fc chimera (Sino Biological) and RetroNectin (Takara Bio Inc). The medium was changed every 2-3 days during this culture period. MEMα (Thermo Fisher Scientific (Gibco)) supplemented with 15% FBS, 4 mM L-glutamine, 100 U/ml penicillin, 100 µg/ml streptomycin, 55 µM 2-mercaptoethanol, 50 µg/ml ascorbic acid 2-phosphate, 10 µg/ml human insulin, 5.5 µg/ml human transferrin, 6.7 ng/ml sodium selenite, 50 ng/ml SCF, 50 ng/ml IL-7, 50 ng/ml Flt3L, 100 ng/ml TPO, 15 µM SB203580, 30 nM SDF-1a was used as the medium to culture these cells. On Day 21, the cells were passaged to new 15 cm dishes freshly coated with hDLL4/RetroNectin. On Day 28, the cells were further passaged to new 15 cm dishes freshly coated with hDLL4/RetroNectin. On Day 35, all cells including CD4/CD8 cells, among others, ("DP cell bulk") were harvested.

Example 3. Differentiation of DP Cell Bulk to NK Cell Bulk

On Day 35, DP cell bulk, i.e., cells obtained from example 2 without undergoing any cell isolation, was seeded in a 48-well plate at $1 \times 10^6$ cells/well, and cultured under 5% $CO_2$ at 37° C. for three days. MEM medium supplemented with 15% FBS, 4 mM L-glutamine, 100 U/ml penicillin, 100 ng/ml streptomycin, 50 µg/ml ascorbic acid 2-phosphate, 10 µg/ml human insulin, 5.5 µg/ml human transferrin, 6.7 ng/ml sodium selenite, 500 ng/ml anti-CD3 antibody (UCHT1), 10 ng/ml IL-2, and 10 ng/ml IL-7 was used as a culture medium. On Day 38, the cells were dispersed in another MEMα medium supplemented with 15% FBS, 4 mM L-glutamine, 100 U/ml penicillin, 100 ng/ml streptomycin, 50 µg/ml ascorbic acid 2-phosphate, 10 µg/ml human insulin, 5.5 µg/ml human transferrin, 6.7 ng/ml sodium selenite, 10 ng/ml IL-2, and 10 ng/ml IL-7 was used as a culture medium. On Day 42, all cells including NK cells ("NK cell bulk") were harvested.

Example 4. Flow Cytometry Analysis

The NK cell bulk was then stained with a set of antibodies listed in Table 1, and was analyzed by flow cytometry. As shown in FIG. 1, a portion of CD3 negative NK cell bulk expressed CD56 ("CD56 positive immune cells"). FIG. 1. The CD56 positive and CD3 negative immune cells are natural killer cells (NK cells). Thus, CD56 positive and CD3 negative immune cells were prepared from a HP cell bulk that was derived from an iPS cells (FfI-01s04 strain). A cell expressing CD56 that was obtained in the process above is sometimes referred to as iPS NK cell. The antibodies used for flow cytometry is shown in Table 1.

TABLE 1

| | |
|---|---|
| Anti-CD3 antibody | CD3 BioLegend APC/Cy7 |
| Anti-CD56 antibody | CD56 Biolegend PE |

Example 5. Single Cell RNA Sequence (scRNAseq) Analysis

In order to identify different cell types in the NK cell bulk population (i.e., the cells obtained in the Example 3), a non-linear dimensionality-reduction technique (uniform manifold approximation and projection (UMAP) based on single cell RNA-seq (scRNAseq)) was applied.

Ten thousands cells from NK cell bulk were subjected to single cell RNA-sequencing on the Ilumina NextSeq 500 at Genewiz. Using the SingleR algorithm and manual cluster labeling, the events were classified into four broad cell populations—monocyte, B cell, NK cell and T cell in PBMC samples. The dataset of PBMCs, freely available from 10× Genomics, was used as a control for data analysis.

Figure 2:
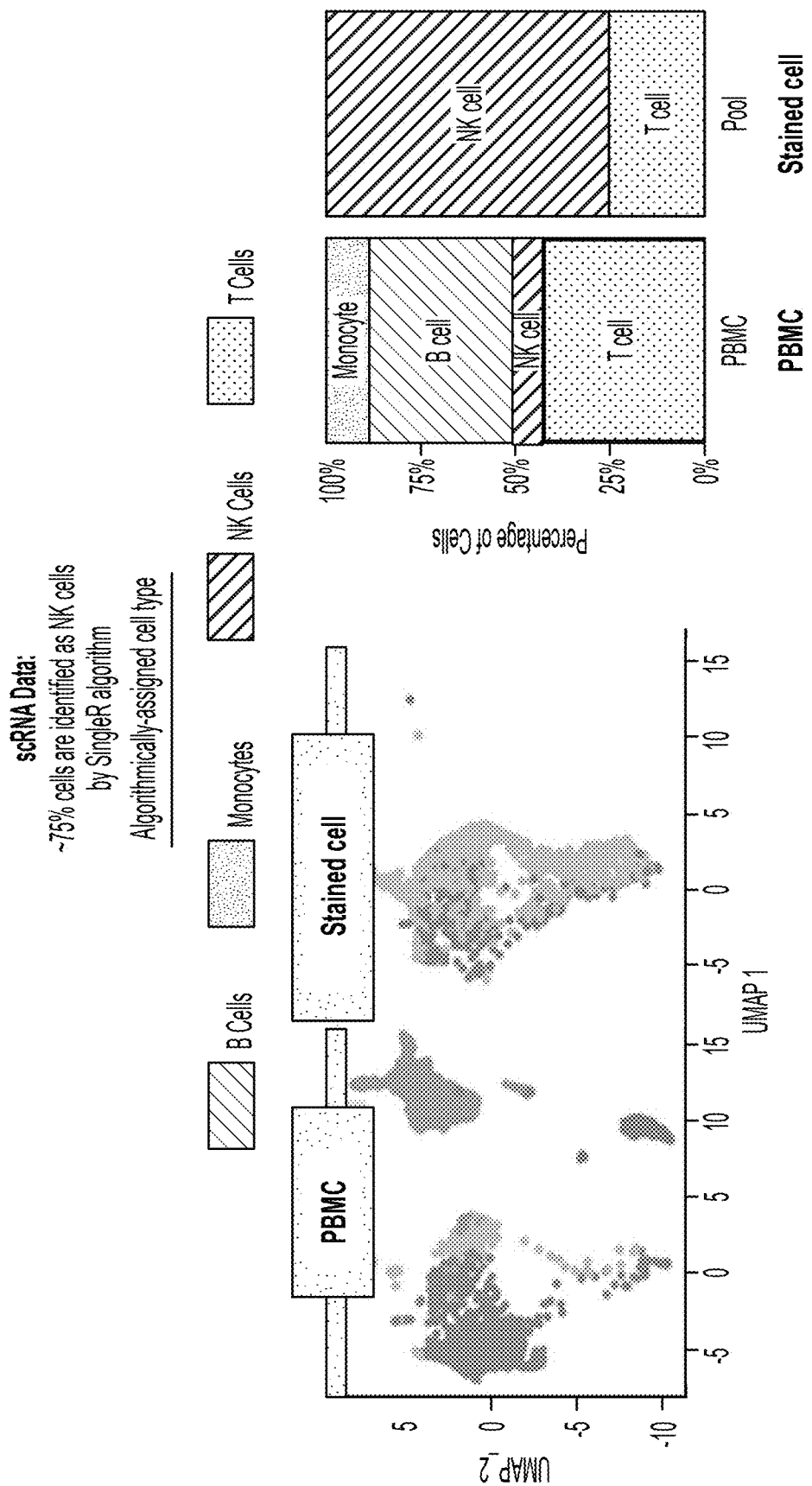
FIG. 2 shows the results of scRNA analysis of a NK cell bulk population that was obtained using the methods described herein. Briefly, iPS cells were cultured as described herein, without an intermediate isolation step. Cells were classified into four cell populations—monocyte, B cell, NK cell and T cell. Approximately 75% of cells in the NK cell bulk population was identified as NK cells (CD56+/CD3− cells), while approximately 25% of cells in the bulk cell population was identified as T cells. The T cells described herein may include NKT cells (CD56+/CD3+ cells).

As shown in FIG. 2, about 75% of the cells in the NK cell bulk were identified as NK cells, while about 25% of the cells in the NK cell bulk were identified as T cells. Thus, the NK cell bulk included both NK cells and T cells based on mRNA profiling by single cell RNA-sequencing.

Example 6. CAR-NK Cell Preparation

NK cells were further modified to express one or more CARs. Modification of NK cells includes steps of: (1) synthesizing an anti-CD19 CAR gene and an IL-15Rα/IL-15 gene; (2) preparing a retrovirus vector containing anti-CD19 CAR gene and IL-15Rα/IL-15 genes; and (3) transducing the NK cells with the retrovirus vector containing anti-CD19 CAR gene and IL-15Rα/IL-15 genes.

CAR/IL15-NK Cell Preparation

Anti-CD19 CAR gene was prepared by synthesizing oligopeptides that are designed to be arranged from N-terminal as shown in Table 2.

TABLE 2

| Sequence from N-terminal | Genes | Number of Amino acids |
|---|---|---|
| 1 | Lead sequence of the heavy chain of an immunoglobulin | 22 |
| 2 | Variable domain in the light chain of the anti-CD19 antibody(FMC60) | 104 |
| 3 | GGGGS linker | 15 |
| 4 | Variable domain in the heavy chain of the anti-CD19 antibody(FMC60) | 120 |
| 5 | CD8 derived sequence (Containing transmembrane domain) | 83 |
| 6 | Intracellular domain of 4-1BB | 47 |
| 7 | Intracellular domain of CD3 zeta | 112 |

An anti-CD19 CAR was constructed in accordance with WO2014/153270, incorporated herein by reference in its entirety.

Preparation IL-15Rα/IL-15 Gene

IL-15Rα/IL-15 gene was prepared by synthesizing oligopeptides that are designed to be arranged from N-terminal. The IL-15Rα/IL-15 was constructed in accordance with Mortier et al., 2006, *The Journal of Biological Chemistry*, Vol 281, No 3, pages 1612-1619 Jan. 20, 2006; Chertova et al., *The Journal of Biological Chemistry*, Vol. 288, No. 25, Pages 18093-18103, Jun. 21, 2013; and Rowley et al., *Eur J Immunol*, 2009 February; 39 (2): 491-506, each of which are incorporated by reference it its entirety.

TABLE 4

| Sequence from N-terminal | Genes | Number of Amino acids |
|---|---|---|
| 1 | Lead sequence of human IL-2 | 23 |
| 2 | C-terminal sequence of human IL-15 | 114 |
| 3 | GGGGS linker | 24 |
| 4 | C-terminal sequence of human IL-15RA | 239 |

Preparation of Retrovirus Vector Containing Anti-CD19 CAR Gene

The anti-CD19 CAR gene was incorporated into a multi-cloning site of a pMY retrovirus vector. The retrovirus vector was generated using FRY-RD18 cells for retrovirus vector production.

Preparation of Retrovirus Vector Containing IL-15Rα/IL-15 Gene

The IL-15Rα/IL-15 gene was incorporated into a multi-cloning site of another pMY retrovirus vector. The retrovirus vector was generated using FRY-RD18 cell for retrovirus vector production.

Transduction of Anti-CD19 CAR Gene and IL-15Rα/IL-15 Gene into iPS NK Cell

The iPS NK cells were transduced with the retrovirus vectors containing anti-CD19 CAR gene and with the retrovirus vectors containing IL-15Rα/IL-15 gene to generate the anti-CD19 CAR expressing iPS NK cell ("iNK-CAR19").

Example 7. In Vivo Anti-Tumor Activity of iNK-CAR19

Luciferase expressing Nalm6 cells (ATCC; cancer cells) ($5 \times 10^5$ cells) were transplanted into NOD/Shi-scid, IL-2R gamma null mice ("NSG mice") via tail vein. The NSG mice, male, 4-5-week-old were sourced from The Jackson Laboratory. Four days after the transplantation of Nalm6 cells, the iNK-CAR19 ($1 \times 10^7$ cells) dispersed in 0.2 ml PBS or just 0.2 ml of PBS without cells were administered to the Nalm6-transplanted NSG mice via tail vein. After the administration of iNK-CAR19 cells or PBS, luciferin was administered to the mice via tail vein. Luciferase activity was measured using IVIS imaging system (PerkinElmer) for over 70 days.

Figure 3:
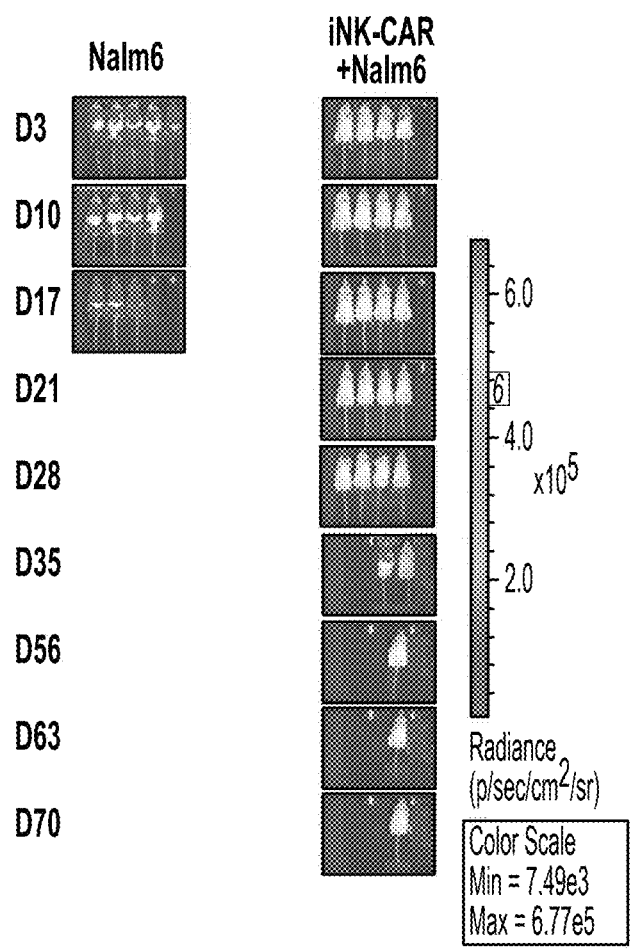
FIG. 3 depicts a series of photographs that show the results of an anti-tumor activity assay in NSG (NOD/Shi-scid, IL-2R gamma null) mice administered luciferase expressing Nalm6 cells, followed by the administration of iNK-CAR19 cells in. Nalm6 cells-transplanted NSG mice were treated with (a) PBS buffer (b) iNK-CAR cells, and anti-tumor efficacy of these treatments was observed. The data shows that iNK-CAR cells reduced proliferation of Nalm6 cells.

FIG. 3 shows the anti-tumor efficacy of untreated (treated with buffer only) and iNK-CAR19 cell treated Nalm6-transplanted NSG mice. Just after three days, luminescence was detected in all the mice treated with D-PBS buffer. In contrast, luminescence was not detected in other mice (treated with either primary CAR T cells or iNK-CAR cells) until 28 days after administration, and luminescence was not detected in one mouse treated with iNK-CAR19 cells even 70 days after the treatment. Thus, iNK-CAR19 cells clearly demonstrated an enhanced toxicity against Nalm6 cancer cells.

EQUIVALENTS AND SCOPE

Those skilled in the art will recognize, or be able to ascertain using no more than routine experimentation, many equivalents to the specific embodiments of the invention described herein.

We claim:

1. A method of producing pluripotent stem cell-derived natural killer (NK) cells comprising:
   (A) providing a bulk cell population in a bulk cell medium, comprising hematopoietic progenitor cells (HPC) (HP cell bulk) derived from pluripotent stem cells;
   (B) culturing HP cell bulk in a CD4/CD8 induction medium comprising a p38 inhibitor and SDF-1 to obtain a heterogeneous population of CD4+/− cells and CD8+/− cells (DP cell bulk);
   (C) culturing the DP cell bulk in NK induction medium comprising IL-2 or IL-7 to obtain NK cells; wherein step (C) does not include a step of isolating CD4+/CD8+ cells from the DP cell bulk and wherein >50% of the cells produced from step (C) are NK cells.

2. The method of claim 1, wherein the method does not include a cell isolation step in step (B).

3. The method of claim 1, wherein the HP cell bulk in step (A) comprises CD34+ cells.

4. The method of claim 1, wherein the DP cell bulk of step (B) comprises an intermediate heterogeneous cell population comprising CD4−/CD8− cells, CD4−/CD8+ cells, CD4+/CD8− cells, and CD4+/CD8+ cells.

5. The method of claim 1, wherein step (B) does not include a step of isolating CD4+/CD8+ cells.

6. The method of claim 1, wherein step (A) comprises culturing pluripotent stem cells in HPC induction media to produce the HP cell bulk.

7. The method of claim 1, wherein the pluripotent stem cell is an induced pluripotent stem cell (iPSC).

8. The method of claim 4, wherein the CD4/CD8 induction media further comprises a compound selected from the group consisting of ascorbic acid, stem cell factor (SCF), IL-7, Flt3L, thrombopoietin (TPO), and combinations thereof.

9. The method of claim 4, wherein the NK induction media of step (C) further comprises a CD3 activator.

10. The method of claim 1, wherein each of the culturing steps is performed at 3-6% oxygen.

11. The method of claim 6, wherein culturing pluripotent stem cells in the HPC induction medium to obtain HP cell bulk lasts for greater than 6 days.

12. The method of claim 7, wherein the iPSC is obtained from peripheral blood mononuclear cells.

13. The method of claim 1, wherein at least 70% or more of CD56+/CD3− cells are produced without a step of enrichment.

14. The method of claim 1, wherein the NK cells are genetically modified to express one or more chimeric antigen receptors (CAR).

15. A method of producing induced pluripotent stem cell (iPSC)-derived natural killer (NK) cells comprising the following steps:
   (1) culturing iPSC in HPC induction media comprising at least one compound selected from vascular endothelial growth factor (VEGF), basic fibroblast growth factor (bFGF), and ascorbic acid to obtain a heterogeneous population of cells comprising hematopoietic progenitor cells (HPC) (HP cell bulk);
   (2) culturing the HP cell bulk obtained in (1) in CD4/CD8 induction media comprising ascorbic acid, p38 inhibitor and SDF-1 to obtain an intermediate heterogeneous population of CD4+/− and CD8+/− cells (DP cell bulk); and
   (3) culturing the DP cell bulk from (2) in NK induction media comprising a compound selected from the group consisting of a CD3 activator, IL-2 and IL-7 to obtain NK cells; and wherein step (3) does not include a step of isolating CD4+/CD8+ cells from the DP cell bulk and wherein >50% of the cells produced from step (3) are NK cells.

16. The method of claim 1, wherein at least 60% of the cells produced from step (C) are NK cells.

* * * * *